US007462466B2

(12) United States Patent
Morgan et al.

(10) Patent No.: US 7,462,466 B2
(45) Date of Patent: Dec. 9, 2008

(54) PORCINE CD59 NUCLEIC ACIDS AND CELLS CONTAINING THE SAME

(75) Inventors: Bryan Paul Morgan, Cardiff (GB); Neil Kevin Rushmere, Cardiff (GB); Stewart James Hinchliffe, Cardiff (GB); Carmen Wilma Van Den Berg, Cardiff (GB)

(73) Assignee: University of Wales College of Medicine (GB)

( * ) Notice: Subject to any disclaimer, the term of this patent is extended or adjusted under 35 U.S.C. 154(b) by 508 days.

(21) Appl. No.: 10/759,181

(22) Filed: Jan. 20, 2004

(65) Prior Publication Data

US 2004/0163140 A1    Aug. 19, 2004

Related U.S. Application Data

(62) Division of application No. 09/673,032, filed as application No. PCT/GB99/01085 on Apr. 8, 1999, now abandoned.

(30) Foreign Application Priority Data

Apr. 9, 1998    (GB)    ................. 9807520.3

(51) Int. Cl.
*C12N 5/10* (2006.01)
*C12N 1/21* (2006.01)
*C12N 1/15* (2006.01)
*C12N 5/16* (2006.01)
*C12N 5/22* (2006.01)
*C12N 15/63* (2006.01)
*C12N 15/12* (2006.01)

(52) U.S. Cl. ................. 435/69.1; 435/325; 435/363; 435/366; 435/252.3; 435/254.11; 435/320.1; 536/23.1; 536/23.5

(58) Field of Classification Search ................. None
See application file for complete search history.

(56) References Cited

FOREIGN PATENT DOCUMENTS

| WO | WO 95/23512 | 9/1995 |
| WO | 97/12035 | 4/1997 |
| WO | WO 97/20937 | * 6/1997 |

OTHER PUBLICATIONS

Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
Bork, 2000, Genome Research 10:398-400.*
Skolnick et al., 2000, Trends in Biotech. 18(1):34-39.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Ruiz-Arguelles et al., 2007, Autoimmunity Reviews 6:155-161.* van den Berg et al., "A rapid method for the isolation of analogues of human CD59 by preparative SDS-PAGE: application topig CD59" Journal of Immunological Methods 179 (1995) 223-231.
van den Berg et al., "Complement-Inhibiting Activities of Human CD59 and Analogues from Rat, Sheep, and Pig are not Homologously Restricted" copyright 1994 by The American Association of Immunologists.
Abstract: PMID: 9507491 Couser, "Pathogenesis of glomerular damage in glomerulonephritis" Nephrol Dial Transplant. 1998; 13 Suppl 1:10-5.
Abstract: PMID: 7688580 Moutabarrik et al., "Cytokine-mediated regulation of the surface expression of complement regulatory proteins, CD46(MCP), CD55(DAF), and CD59 on human vascular endothelial cells" Lymphokine Cytokine Res. Jun. 1993; 12(3):167-72.
Abstract: PMID: 9048341 Nangaku et al., "Overexpression of Crry protects mesangial cells from complement-mediated injury" J Am Soc Nephol. Feb. 1997; 8(2):223-33.
Abstract: PMID: 8807596 Nangaku et al., "Transfected CD59 protects mesangial cells from injury induced by antibody and complement" Kidney Int. Jul. 1996; 50(1):257-66.
Abstract: PMID: 7812736 Schieren et al., "Expression of the complement regulator factor C8 binding protein on human glomerular cells protects them from complement-mediated killing" Exp Nephrol. Sep.-Oct. 1994; 2(5):299-305.
Liszewski et al. Annul. Rev. Immunol. vol. 9, pp. 431-455, 1991.
Yoko et al. Journal of Biological Chemistry, 277:26729-26732, 2002.
Caras et al. Nature 325(6104):545-549, 1987.
C.W. Van Den Berg and B.P. Morgan, "Complement-Inhibiting Activities of Human CD59 and Analogues from Rat, Sheep, and Pig are not Homologously Restricted," Journal of Immunology, vol. 152, No. 8, Apr. 15, 1994, XP002122369, p. 4100-4101.
C.W. Van Den Berg, R.S. Harrison and B.P. Morgan, "A Rapid Method for the Isolation of Analogues of Human CD59 by Preparative SDS-Page: Application to Pig CD59," Journal of Immunological Methods, vol. 179, 1995, 223-231,XP002122370.
N.K. Rushmere, S. Tomlinson and B.P. Morgan, "Expression of Rat CD59: Functional Analysis Confirms Lack of Species Selectivity and Reveals that Glycosylation is not Required for Function." Immunology, vol. 90, No. 4, Apr. 1997, pp. 640-646, XP002122371.
Hinchliffe et al., "Molecular Cloning and Functional Characterization of the Pig Analogue of CD59: Relevance to Xenotransplantation", Journal of Immunology, 1998, vol. 160, No. 8, XP-002350939, pp. 3924-3932.
Rushmere et al., "Molecular cloning of the rat analogue of human CD59: structural comparison with human CD59 and identification of a putative active site", The Biochemical Journal, 1994, vol. 304, XP-002350940, pp. 595-601.
Byrne et al., abstract of "Transgenic pigs expressing human CD59 and decay-accelerating factor produce an intrinsic barrier to complement-mediated damage", Transplantation, 1997, vol. 63, No. 1, pp. 149-155.
Morgan, abstract of "Complement regulatory molecules: application to therapy and transplantation", Immunology Today, 1995, vol. 16, No. 6, pp. 257-259.

* cited by examiner

*Primary Examiner*—Elizabeth C. Kemmerer
(74) *Attorney, Agent, or Firm*—King & Spalding

(57) ABSTRACT

A graftable animal cell or tissue of a donor species for use in medicine expresses, or is capable of being caused to express, increased amounts of endogenous complement regulatory molecules for preventing activation of complement in a recipient species. Such tissue or organs are useful for xenotransplantation. Porcine complement regulatory proteins CD59, DAF have been sequenced. Also disclosed are methods of inducing in an animal cell or tissue resistance protection against complement attack.

10 Claims, 29 Drawing Sheets

```
GAAA
 -4

AGACGCGCAGGCCGGGCCGCTCTCCCGACGGGGAGTAGCGCTGCAGCCGGACGCAGGGTGCAGTTA
         10        20        30        40        50        60
```

|  |  |  |  | M | G | S | K | G | G | F | I | L | L | W | L | -14 |
|--|--|--|--|--|--|--|--|--|--|--|--|--|--|--|--|--|
| GAATCCATAGACGGTCACG | | | | ATG | GGA | AGC | AAA | GGA | GGG | TTC | ATT | TTG | CTC | TGG | CTC | |
| 70 | | 80 | | | 90 | | 100 | | | 110 | | | 120 | | | |

| L | S | I | L | A | V | L | C | H | L | G | H | S | ⌐L⌐ | Q | C | Y | 4 |
|--|--|--|--|--|--|--|--|--|--|--|--|--|--|--|--|--|--|
| CTG | TCC | ATC | CTG | GCT | GTT | CTC | TGC | CAC | TTA | GGT | CAC | AGC | CTG | CAG | TGC | TAT | |
| | | 130 | | | 140 | | | 150 | | | 160 | | | | 170 | | |

ψ

| N | C | I | N | P | A | G | S | C | T | T | A | M | N | C | S | H | 21 |
|--|--|--|--|--|--|--|--|--|--|--|--|--|--|--|--|--|--|
| AAC | TGT | ATC | AAC | CCA | GCT | GGT | AGC | TGC | ACT | ACG | GCC | ATG | AAT | TGT | TCA | CAT | |
| | | 180 | | | 190 | | | 200 | | | 210 | | | 220 | | | |

| N | Q | D | A | C | I | F | V | E | A | V | P | P | K | T | Y | Y | 38 |
|--|--|--|--|--|--|--|--|--|--|--|--|--|--|--|--|--|--|
| AAT | CAG | GAT | GCC | TGT | ATC | TTC | GTT | GAA | GCC | GTG | CCA | CCC | AAA | ACT | TAC | TAC | |
| | 230 | | | 240 | | | 250 | | | 260 | | | 270 | | | | |

| Q | C | W | R | F | D | E | C | N | F | D | F | I | S | R | N | L | 55 |
|--|--|--|--|--|--|--|--|--|--|--|--|--|--|--|--|--|--|
| CAG | TGT | TGG | AGG | TTC | GAT | GAA | TGC | AAT | TTC | GAT | TTC | ATT | TCG | AGA | AAC | CTA | |
| | 280 | | | 290 | | | 300 | | | 310 | | | 320 | | | | |

ψ

| A | E | K | K | L | K | Y | N | C | C | R | K | D | L | C | N | K | 72 |
|--|--|--|--|--|--|--|--|--|--|--|--|--|--|--|--|--|--|
| GCG | GAG | AAG | AAG | CTG | AAG | TAC | AAC | TGC | TGC | CGG | AAG | GAC | CTG | TGT | AAC | AAG | |
| | 330 | | | 340 | | | 350 | | | 360 | | | 370 | | | | |

⇓

| S | D | A | T | I | S | S | G | K | T | A | L | L | V | I | L | L | 89 |
|--|--|--|--|--|--|--|--|--|--|--|--|--|--|--|--|--|--|
| AGT | GAT | GCC | ACG | ATT | TCA | TCA | GGG | AAA | ACC | GCT | CTG | CTG | GTG | ATC | CTG | CTG | |
| | 380 | | | 390 | | | 400 | | | 410 | | | 420 | | | | |

| L | V | A | T | W | H | F | C | L | * | | | | | | | | 98 |
|--|--|--|--|--|--|--|--|--|--|--|--|--|--|--|--|--|--|
| CTG | GTA | GCA | ACC | TGG | CAC | TTT | TGT | CTC | TAA | | | | | | | | |
| | 430 | | | 440 | | | 450 | | | | | | | | | | |

```
CTGTACACCAGGAGAGTTTCTCCTCAACTTCCTCTGTCTCTCTGTTCCTATTTCCCATGCTGCGGTGTT
  460       470       480       490       500       510       520
CCAAAGGCTGTGTATGCTCCAGCTTCTTCCTGTTGGGAAGGACTAAACCTAGCTTGAGCACTTTGGATT
  530       540       550       560       570       580       590
AGAGAGAGAAACTTTGAGCGACTTTGAAGACCAGGCCTGTTGGCAGAGAAGACCTGTCAGAGGGGAAAC
  600       610       620       630       640       650       660
GTTTTAAGAGTGAAGCACAGGTGATTTGAGCGAGGCCTATGCGTCTTCCTCTGCTCTTGGCAGGACCAG
  670       680       690       700       710       720       730
CTTTGCGGTAACCATTCGATAGATTCCACAATCCTT
  740       750       760
```

*Fig 2*

```
      -20            -10             1            10            20            30
PIG:  MGSKGGFILLWLLSILAVLCHLGHSLQCYNCINP-AGSCTTAMNCSHNQDACIFVEAVPPKTYYQ
      |||  |  ||  |   ||| ||||||| || |||| ||   | |||  | |||  |   |   |
HUM:  MGIQGGSVLFGLLLVLAVFCHSGHSLQCYNCPNP-TADCKTAVNCSSDFDACLITKAGLQVYN-K
      ||   | ||  ||| || |||||||||||| ||| |||||| |||||| |||||||| |||| |
RAT:  MRARRGFIL--LLL-LAVLCSTGVSLRCYNCLDP-VSSCKTNSTCSPNLDACLVAVSGKQVYQ-Q
      |  ||| || ||| ||| ||| |||| ||||| | |||||||| || || || |  ||| || |
MUR:  MRAQRGLIL--LLLLAVFCSTAVSLTCYHCFQPVVSSCNMNSTCSPDQDSCLYAVAGMQVYQ-R 40            50            60            70            80            90
PIG:  CWRFDECNFDFISRNLAEKKLKYNCCRKDLCNKSD-----ATIS-SGKTALL-VILLLVATWHFCL.
      |||||||||||||||||||||||||||||||||||      ||| ||||||| ||||||||| |||
HUM:  CWKFEHCNFNDVTTRLRENELTYYCCKKDLCNFNEQLEN--GGTSLSEKTVLLLVTPFLAAAWSLHP.
      || | |||||  |  ||||| | |||| |||||       |||| ||||||| || ||||| | |
RAT:  CWRFSDCNAKFILSRLEIANVQYRCCQADLCNKSFEDKPNNGAISLLGKTALL-VTSVLAAILKPCF.
      ||  |||   ||  | ||   | ||  |||||         ||| ||||||| || ||||||| ||
MUR:  CWKQSDCHGEIIMDQLEETKLKFRCCQFNLCNKSD-----GS-LGKTPLLGTSVLVAIL-NLCFLSHL.
      ||  |||   | |  |||  ||  || |||||          |||| ||| || ||   |||||
RAB:  CWRYEDCNFFEFISNRLEENSLKYNCCRKDLCNGPEDDGTAL----TGRTVLL-VAPLLAAARNLCL
```

*Fig. 4*

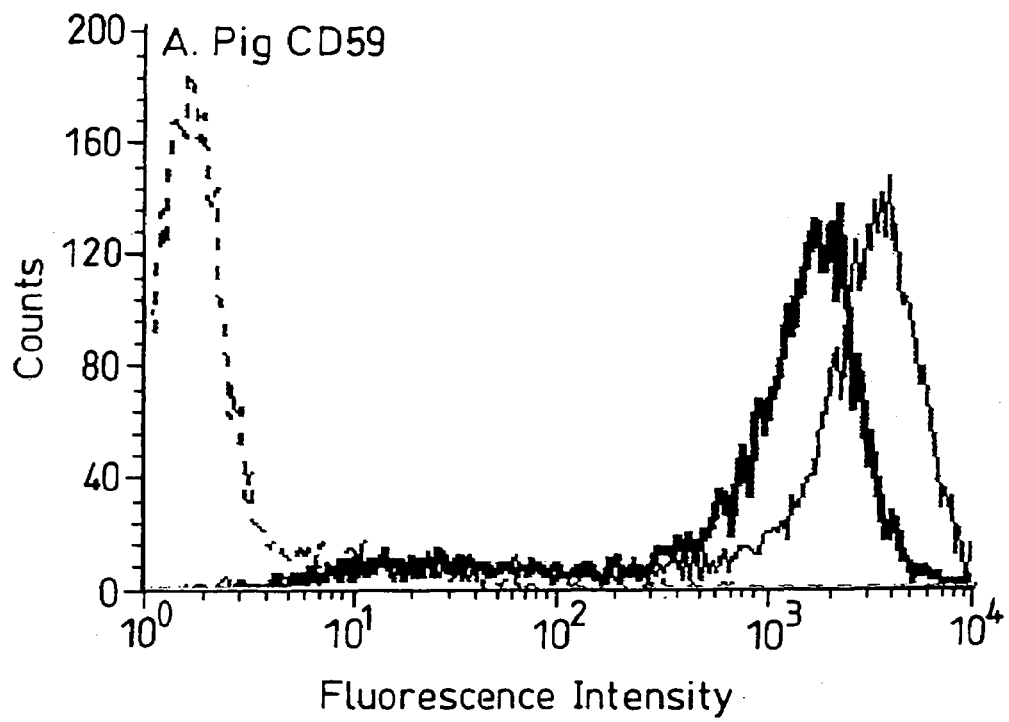
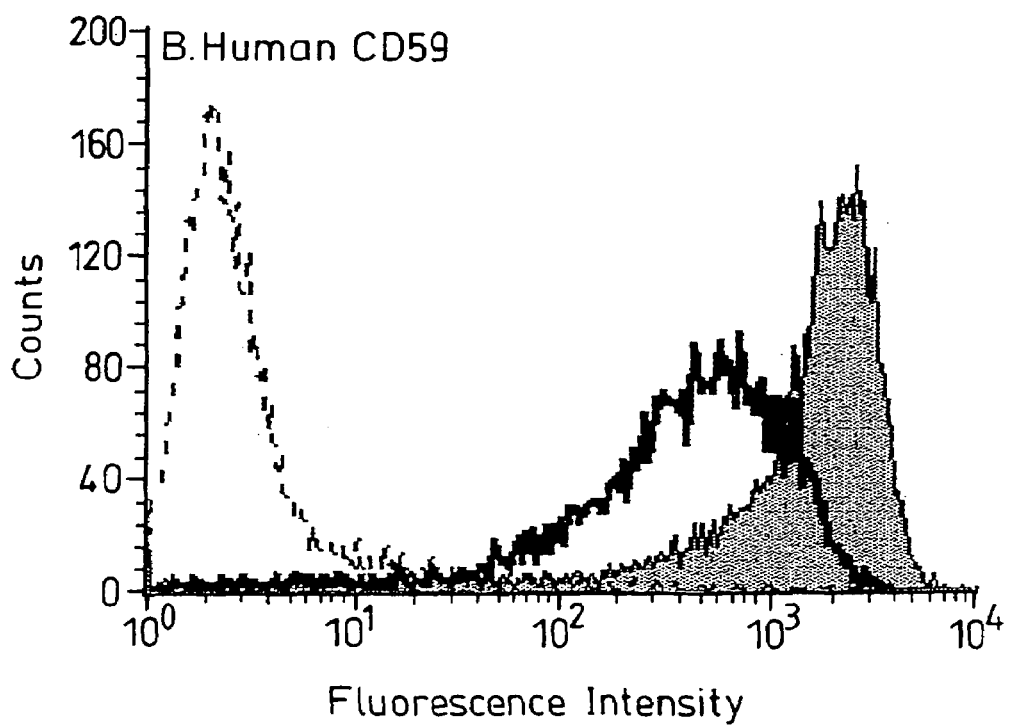
Fig 5

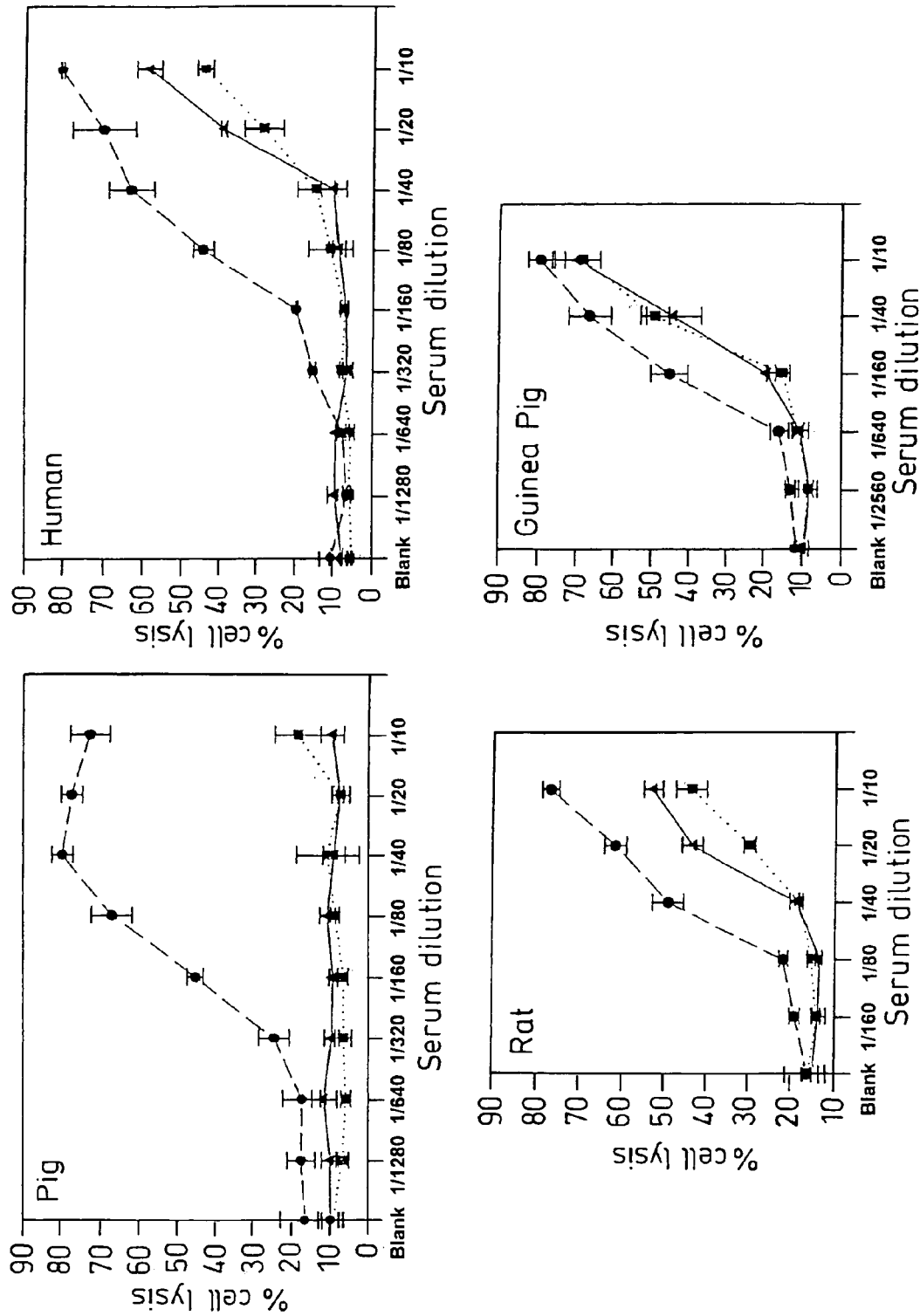
Fig. 7 (part 1 of 2)

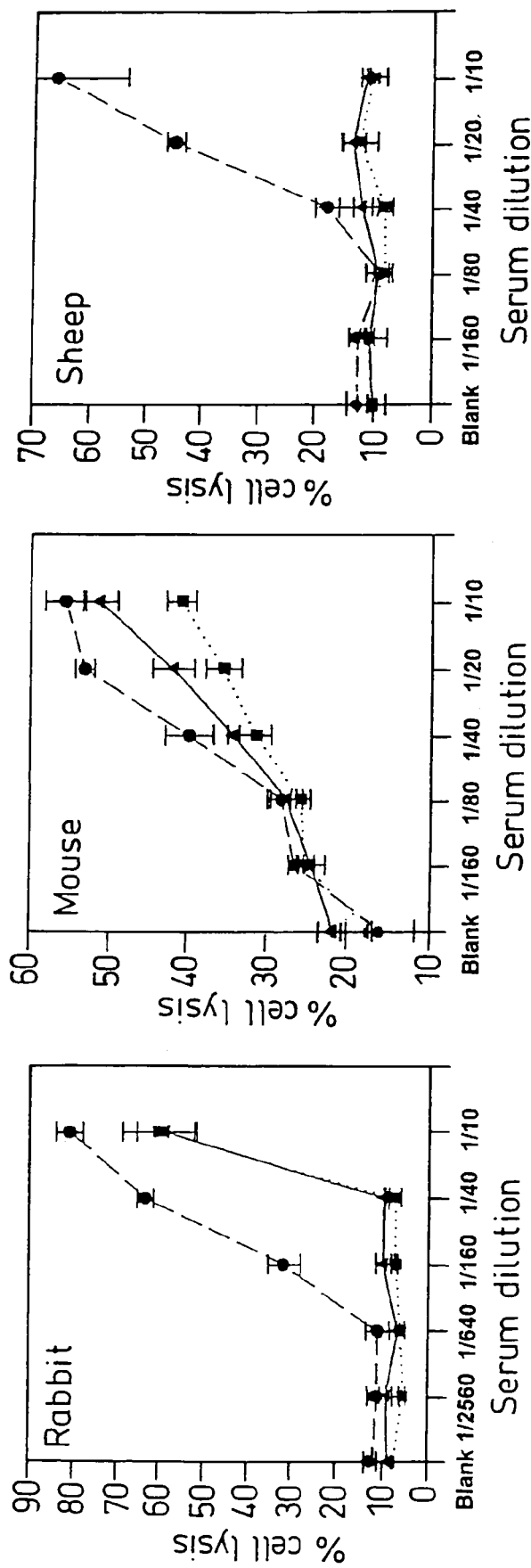
Fig. 7 (part 2 of 2)

Dose/response Cofactor activity: pig MCP vs Hu sMCP 500 ng C3 was incubated with 50 ng factor I and various amounts of pig MCP or human sMCP for 16 at 37°C. W.blot of reduced samples, probed with anti Hu C3c Pig MCP is a better cofactor than Hu sMCP for human C3 and human factor I

Fig. 11 Inhibition of CP and AP of human serum by human sMCP and pig MCP
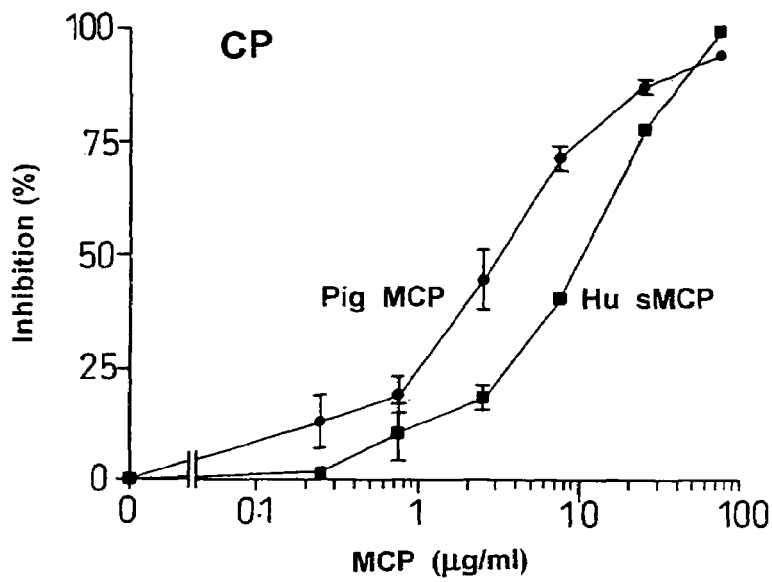
RaE were incubated with human serum in the presence of Hu soluble MCP or pig MCP under CP or AP conditions.
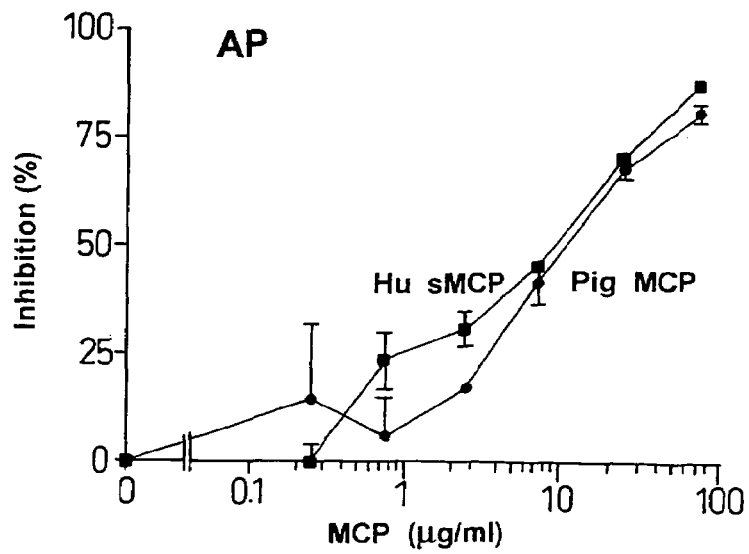
Pig MCP is a better regulator of the CP of human C than human sMCP.
Pig MCP and Hu sMCP have similar activity in regulation of the human AP.

pDAF-7 cDNA sequence:

```
CCACCGCGGTGGCGGCNCGCTCTAGAACTAGTGGATCCCCCGGGCTGCAG
GAATTCGGCACGAGATTTCGTCTTAATCGCGGAGGTCGCAGAGTCCGGGA
GCCGCTCGGGGTCCCCGTTCCCGCGCGCCATGAGTCCCCTGCCGCGGAGC
GCCCCCGCGGTGAGGCGCCTAATGGGCGGACAGACGCCGCCGCCGCTGCT
GCTGCTGCTGCTGCTGTGTATCCCGGCTGCGCAGGGTGACTGCAGCC
TTCCACCCGATGTACCTAATGCCCAACCAGATTTGCGAGGTCTTGCAAGT
TTTCCTGAACAAACCACAATAACATACAAATGTAACAAAGGCTTTGTCAA
AGTTCCTGGCATGGCAGACTCAGTGCTCTGTCTTAATGATAAATGGTCAG
AAGTTGCAGAATTTTGTAATCGTAGCTGTGATGTTCCAACCAGGCTACAT
TTTGCATCTCTTAAAAAGTCTTACAGCAAACAGAATTATTTCCCAGAGGG
TTTCACCGTGGAATATGAGTGCCGTAAGGGCTATAAAAGGGATCTTACTC
TATCAGAAAAACTAACTTGCCTTCAGAATTTTACGTGGTCCAAACCTGAT
GAATTTTGCAAAAAAAAACAATGTCCGACTCCTGGAGAACTAAAAAATGG
TCATGTCAATATAACAACTGACTTGTTATTTGGCGCATCCATCTTTTTCT
CATGTAACGCAGGGTACAGACTAGTTGGTGCAACTTCTAGTTACTGtTTT
GCCATAGCAAATGATGTTGAGTGGAGTGATCCATTGCCAGATTGCCAAGA
AATTTCTCCAACTGTCAAAGCCATACCAGCTGTTGAGAAACCCATCACAG
TAAATTTTCCAGCAACAAAGTATCCAGCTATTCCCAGGGCCACAACGAGT
TTTCATTCAAGTACATCTAAAAATCGAGGAAACCCTTCTTCAGGCATGAG
AATCATGTCGTCTGGTACCATGCTACTTATTGCAGGAGGTGTTGCTGTTA
TTATAATAATTGTTGCCCTAATTCTAGCCAAAGGTTTCTGGCACTATGGA
AAATCAGGCTCTTACCACACTCATGAGAACAACAAAGCCGTTAATGTTGC
ATTTTATAATTTACCTGCGACTGGCGATGCCGCAgATGTAAGACCTGGTA
ATTAACAAAAGGACGTGCATGTAACACTGACAGTTTTGCTTATGGTGC
TAGTAACCATTGGCTAGCTGACTTAGCCAAAGAAGAGTTAAGAAGAAAGT
GCACACAAGTACACAGAATATTTTCAGTTTCTTAAAACTTTCAGGTGGGA
GTGGACATAGTTTGTGGTAGTGNTCTTCGNTTTGCATGGTTTCATTGGCT
CTAAGGNACATAGGAATGCACAGAACCNAAGAGAAACAAATCTATCCTGA
AANTACATCCTCAACACTTCTAANACTCTTGGAAATNGAACAAGNTCATA
AGATTGGGAGCAATTACTTTCCCAAAAGGGTGAGAAAAATGGAGAAATTT
GGTCATGGGTAGNAATTTTNGAAAAANGAAACCCNAAAGGGGANTTTTCC
CCCCCAAAGGGGNAAGGGTATTTTTATTTAATTAAGGNAAAAAAAAAAA
AAAAACCCNNNGGGGGGGCCCGGGNCCCATTTTCCCT
``` pDAF-14 cDNA sequence:

```
CACGAGCCGCCGCCGCTGCTGCTGCTGCTGCTGCTGCTGTGTATCCCGGC
TGCGCAGGGTGACTGCAGCCTTCCACCCGATGTACCTAATGCCCAACCAG
ATTTGCGAGGTCTTGCAAGTTTTCCTGAACAAACCACAATAACATACAAA
TGTAACAAAGGCTTTGTCAAAGTTCCTGGCATGGCAGACTCAGTGCTCTG
TCTTAATGATAAATGGTCAGAAGTTGCAGAATTTTGTAATCGTAGCTGTG
ATGTTCCAACCAGGCTACATTTTGCATCTCTTAAAAAGTCTTACAGCAAA
CAGAATTATTTCCCAGAGGGTTTCACCGTGGAATATGAGTGCCGTAAGGG
CTATAAAAGGGATCTTACTCTATCAGAAAAACTAACTTGCCTTCAGAATT
TTACGTGGTCCAAACCTGATGAATTTTGCAAAAAAAAACAATGTCCGACT
CCTGGAGAACTAAAAAATGGTCATGTCAATATAACAACTGACTTGTTATT
TGGCGCATCCATCTTTTTCTCATGTAACGCAGGGTACAGACTAGTTGGTG
CAACTTCTAGTTACTGtTTTGCCATAGCAAATGATGTTGAGTGGAGTGAT
CCATTGCCAGAaTGCCAAGAAATTTCTCCAACTGTCAAAGCCaTACCAGC
TGTTGAGAAACCCATCACAGTAAATTTTCCAGGTACCAAAGCCCTATCAT
CTCCTCAGAAACCCTCCACAGCAAATACTCTAGCTACAGAGTTACTACCA
ACTCCTCAGGAACCCACCACAGTAAATGTTCCAGATAGTAAAGCCATATC
ATCTCCTCAGAAACCCTCCACAGTAAATACTCCAGCTACAGACTTACTAC
CAACTCCTCAGGAACCCACCACAGTAAAtGTTCCAGATAGTAAAGCCATA
TCATCTTCTCAGAAACCCTCCACAGTAAATACTCCAGCTCAGACTTACTA
CCAACTCCTCAGGAACCCACCACAGToA
```

*Fig 14* pDAF-7, predicted protein sequence:

```
MGGQTPPPLLLLLLLLLCIPAAQGDCSLPPDVPNAQPDLRGLASFPEQTTI
TYKCNKGFVKVPGMADSVLCLNDKWSEVAEFCNRSCDVPTRLHFASLKKS
YSKQNYFPEGFTVEYECRKGYKRDLTLSEKLTCLQNFTWSKPDEFCKKKQ
CPTPGELKNGHVNITTDLLFGASIFFSCNAGYRLVGATSSYCFAIANDVE
WSDPLPDCQEISPTVKAIPAVEKPITVNFPATKYPAIPRATTSFHSSTSK
NRGNPSSGMRIMSSGTMLLIAGGVAVIIIVALILAKGFWHYGKSGSYHT
HENNKAVNVAFYNLPATGDAADVRPGN.
``` pDAF-14, predicted protein sequence:

```
   HEPPPLLLLLLLLLCIPAAQGDCSLPPDVPNAQPDLRGLASFPEQTTI
TYKCNKGFVKVPGMADSVLCLNDKWSEVAEFCNRSCDVPTRLHFASLKKS
YSKQNYFPEGFTVEYECRKGYKRDLTLSEKLTCLQNFTWSKPDEFCKKKQ
CPTPGELKNGHVNITTDLLFGASIFFSCNAGYRLVGATSSYCFAIANDVE
WSDPLPECQEISPTVKAIPAVEKPITVNFPGTKALSSPQKPSTANTLATE
LLPTPQEPTTVNVPDSKAISSPQKPSTVNTPATDLLPTPQEPTTVNVPDS
KAISSSQKPSTVNTPAQTYYQLLRNPPQ.
```

Alignment with human DAF (conserved residues marked as *):

```
1           10         20         30         40         50
  PSVPAALPLLGELPRLLLLVLLCLPAVWGDCGLPPDVPNAQPALEGRTS         HuDAF
    ....  ...  ..   ...............  ..   .
MGGQTPP-------PLLLLLLLLLCIPAAQGDCSLPPDVPNAQPDLRGLAS        pDAF-7

51          60         70         80         90        100
FPEDTVITYKCEESFVKIPGEKDSVTCLKGMQWSDIEEFCNRSCEVPTRL         HuDAF
... . ..... ... ..  ... ..    ..  .......  .....
FPEQTTITYKCNKGFVKVPGMADSVLCLND-KWSEVAEFCNRSCDVPTRL         pDAF-7

101         110        120        130        140        150
NSASLKQPYITQNYFPVGTVVEYECRPGYRREPSLSPKLTCLQNLKWSTA         HuDAF
....  .  ......  .  ....... ..  .  .. .......  ..
HFASLKKSYSKQNYFPEGFTVEYECRKGYKRDLTLSEKLTCLQNFTWSKP         pDAF-7

151         160        170        180        190        200
VEFCKKKSCPNPGEIRNGQIDVPGGILFGATISFSCNTGYKLFGSTSSFC         HuDAF
 ......  ..  ...   ..   ....  .... ..  . ...  .
DEFCKKKQCPTPGELKNGHVNITTDLLFGASIFFSCNAGYRLVGATSSYC         pDAF-7

201         210        220        230        240        250
LISGSSVQWSDPLPECREIYCPAPPQIDNGIIQGERDHYGYRQSVTYACN         HuDAF
  .......  ..
FAIANDVEWSDPLPDCQEI-------------------------------         pDAF-7
              ↑end SCR3
251
KGFTMIGEHSIYCTVNNDEGEWSGPPPECRGKSLTSKVPPTVQKPTTVNV         HuDAF
                                   ...  . ... ...
---------------------------------SPTVKAIPAVEKPITVNF        pDAF-7
                                     ↑end SCR4
301
PTTEVSPTSQKTTTKTTTPNAQATRSTPVSRTTKHFHETTPNKGSGTTSG         HuDAF
 .. .         ..                       .     .
PATKYPAIPRATTSFHSSTSKNRGNPSSGMRIMSSGTMLLIAGGVAVIII          pDAF-7
  ↑end STP-A
351
TTRLLSGHTCFTLTGLLGTLVTMGLLT                                HuDAF
      .
IVALILAKGFWHYGKSGSYHTHENNKAVNVAFYNLPATGDAADVRPGN.          pDAF-7
```

*Fig 15*

Northern analysis of porcine DAF

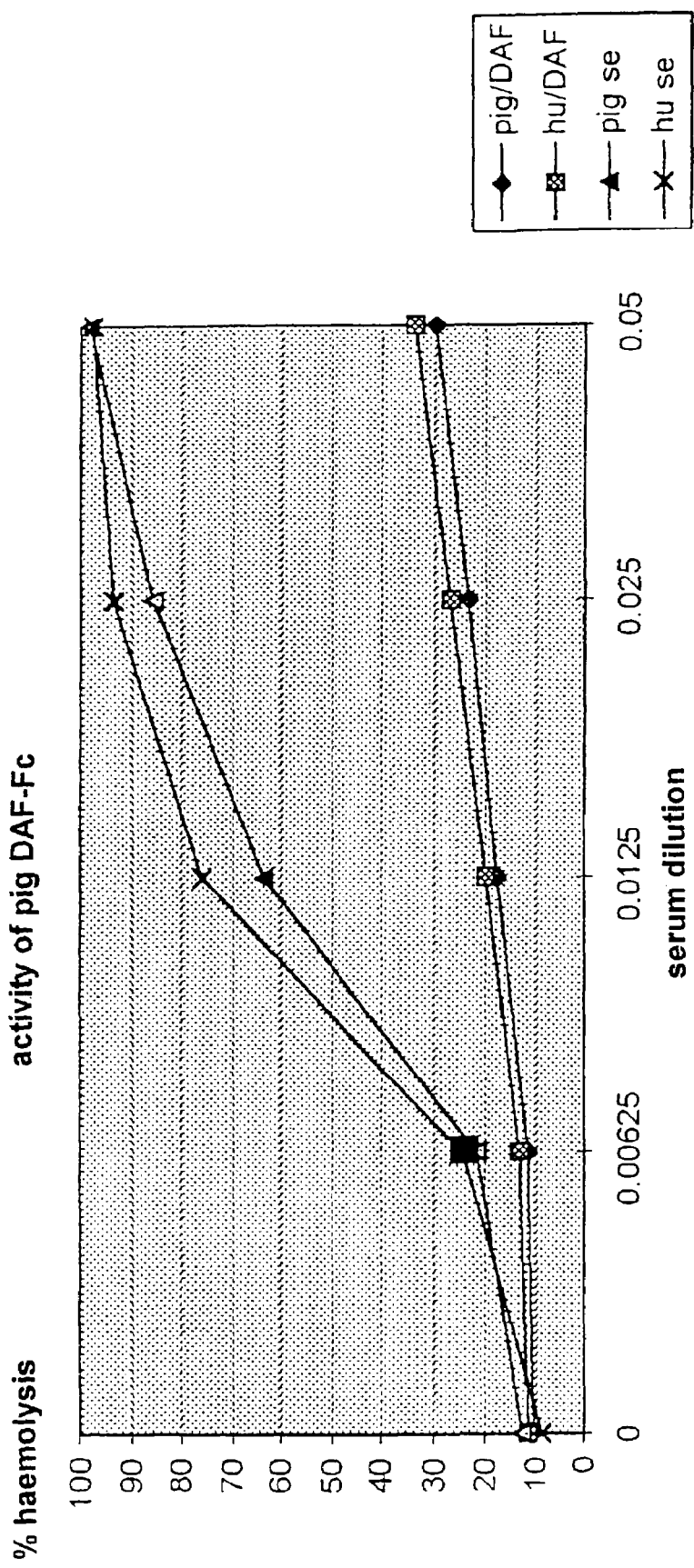
Fig 17a Activity of pig DAF-Fc
Antibody-sensitised human erythrocytes in GVB were incubated for 30 min at 37°C with various dilutions of pig or human serum in the presence or absence of pig DAF-Fc at 10µg/ml (final). Haemolysis was measured by quantifying haemoglobin release into supernatant.

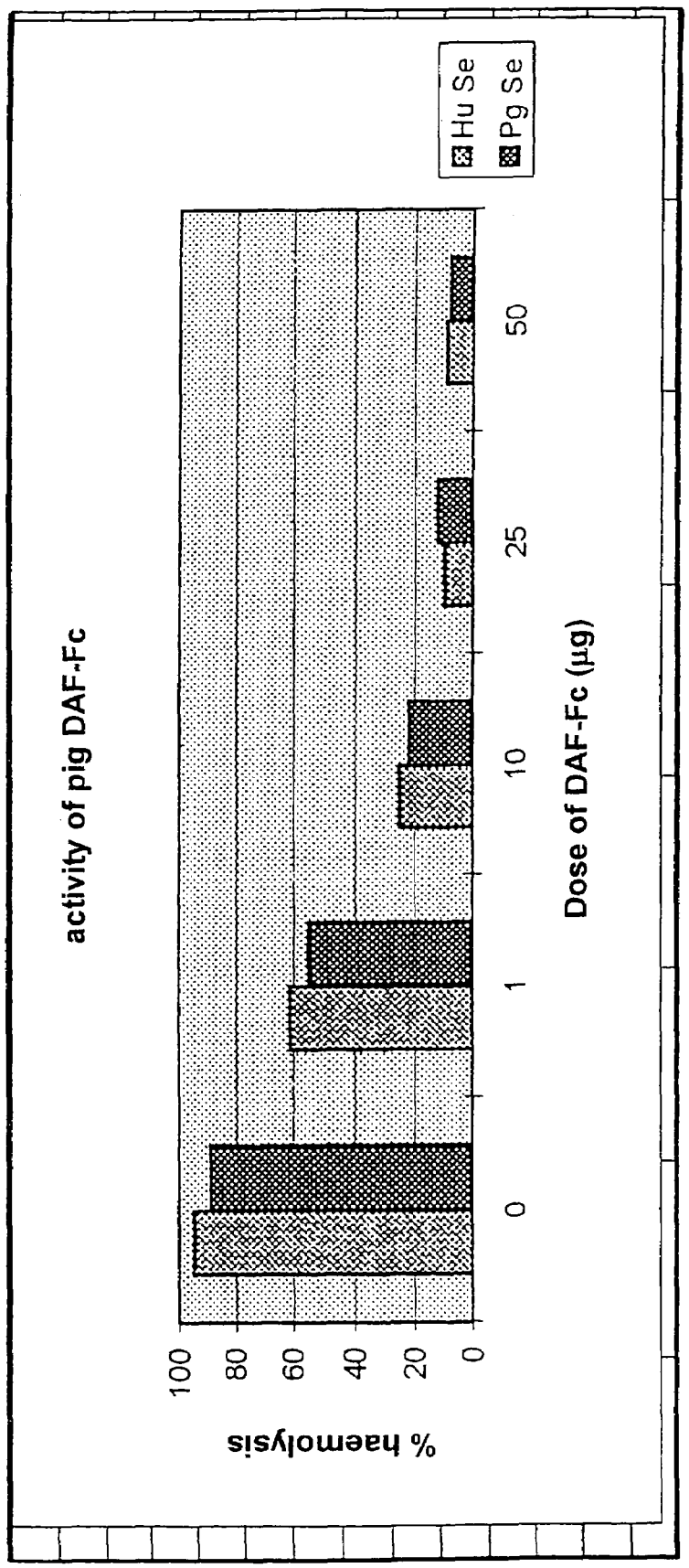
Fig. 17b Activity of pig DAF-Fc - dose response with human and pig serum
Antibody-sensitised human erythrocytes in GVB were incubated for 30 min at 37°C with a constant dilution of human or pig serum (1:20) and various amounts of pig DAF-Fc (0 - 50µg/ml (final)). Haemolysis was measured by quantifying haemoglobin release into supernatant.

Effect of PMA on expression of CD59 and MCP and C-susceptibility of PAEC
Fig 18
PAEC were cultured in the presence of 10 nM PMA. Cells were harvested and analysed for expression of pig CD59 and pig MCP and other cell surface markers and susceptibility to lysis by NHS
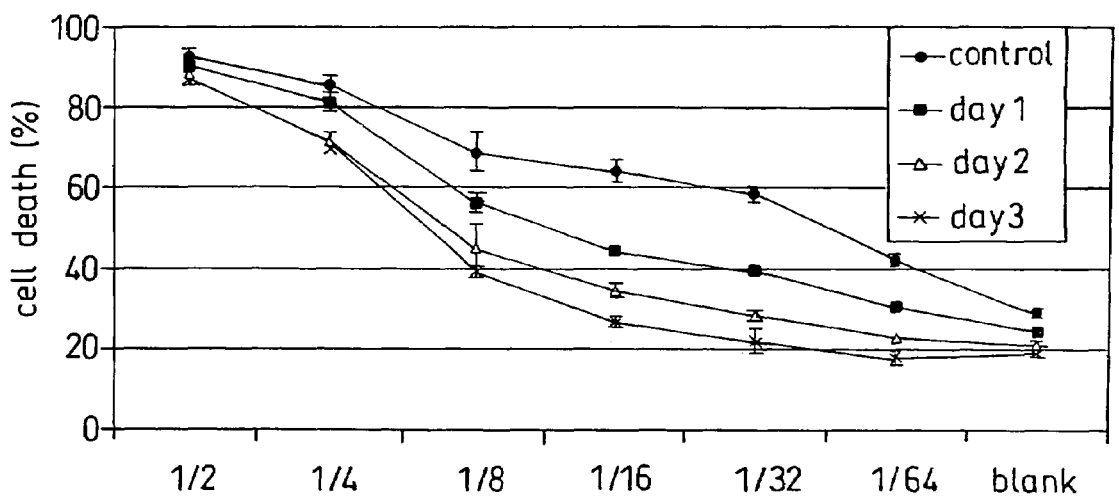
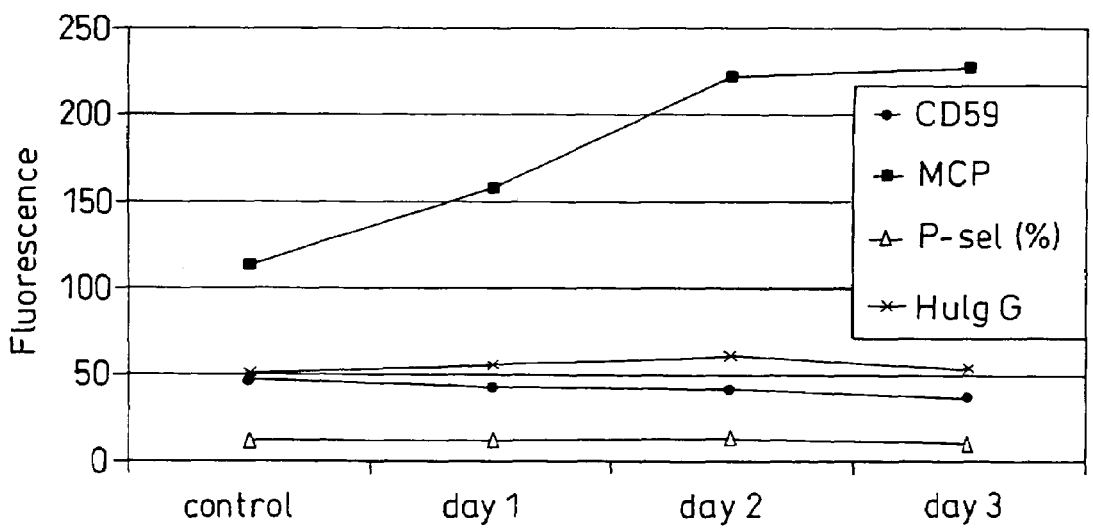

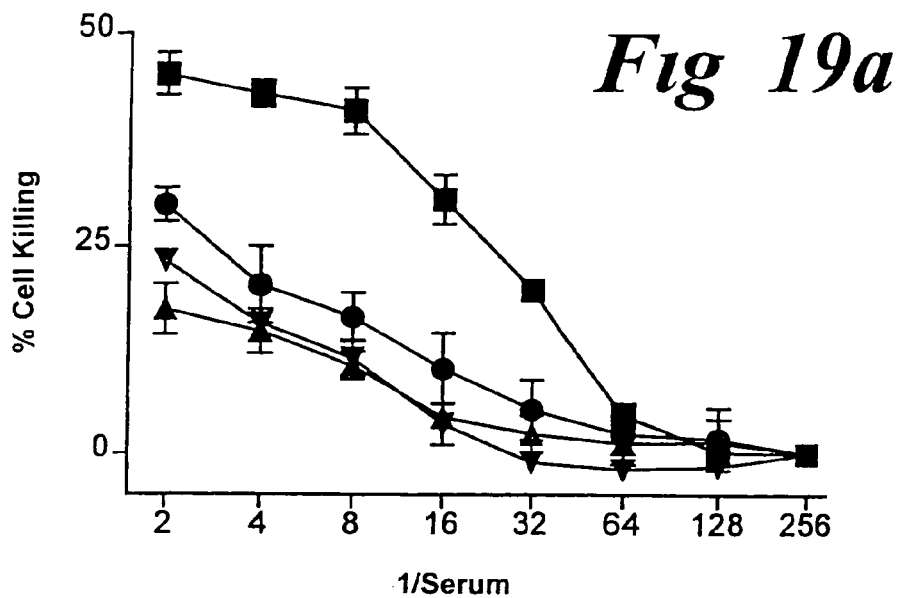

Effect Of Non-Lethal Complement Attack on the Lysis Of PAE cells PAE cells were incubated with 1/20 (▲), 1/30 (▼), 1/40 (●) or zero human serum (■) before being used in a propidium iodide cell killing assayagainst NHS. Values are means of triplicates ± SD.

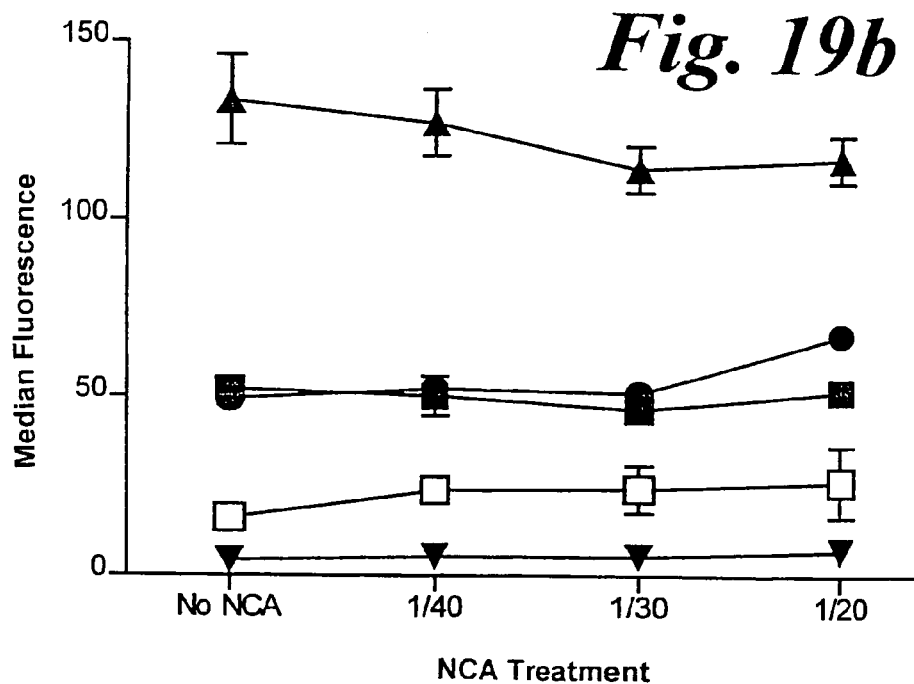

Staining of NCA Treated PAE Cells Sensitised PAE cells were incubated with different non-lethal concentrations of human serum. These cells were the then stained for MCP (■), Human IgG ( ), CD59 (▲), P-selectin (total cells) (□) or P-selectin (positive staining cells) (▼) Values are means of triplicates ± SD.

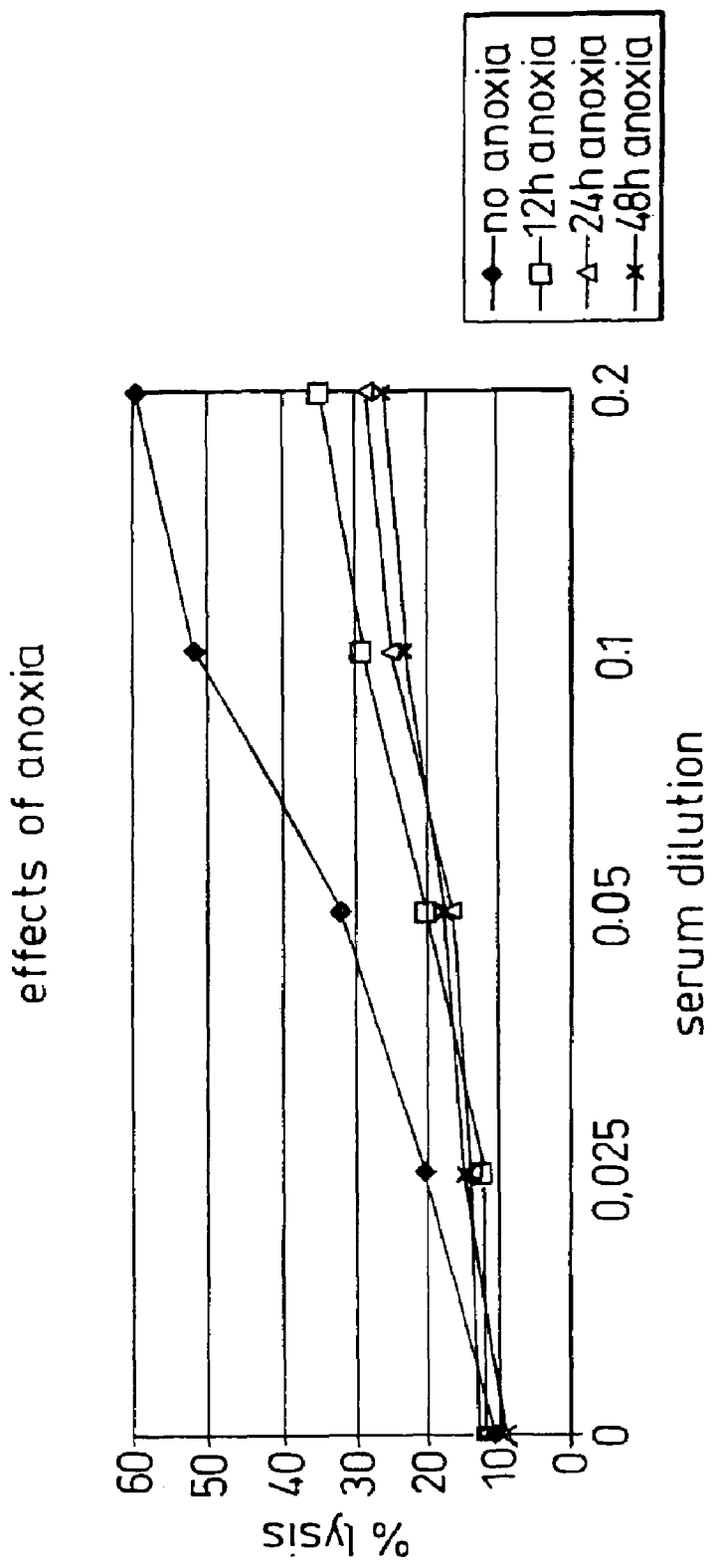
Fig. 20a Effects of anoxia
PAEC were incubated under anoxic conditions at 37°C for 0, 12, 24 or 48 hours. Cells were then subjected to complement attack by exposing to various dilutions of human serum

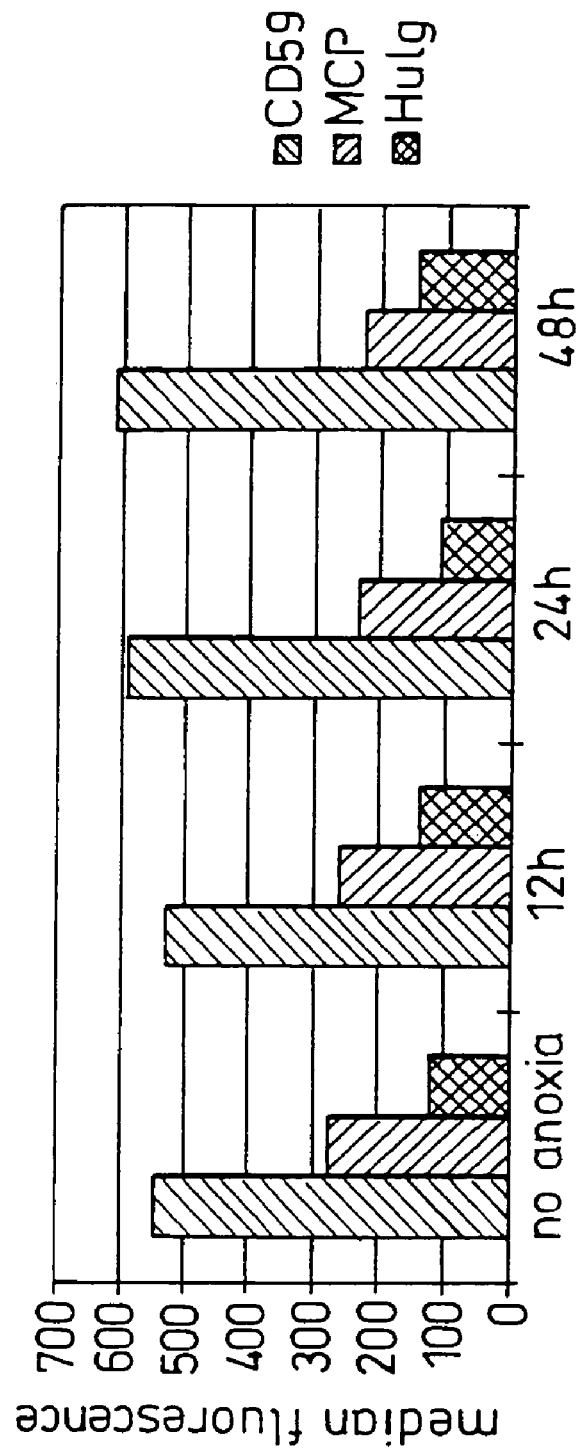
Fig. 20b Effects of anoxia
Effects of anoxia on CRP expression
PAEC were incubated under anoxic conditions at 37° C for 0, 12 24 or 48 hours. Cells were then analysed by flow cytometry for expression of CD59, MCP or binding of HuIg.

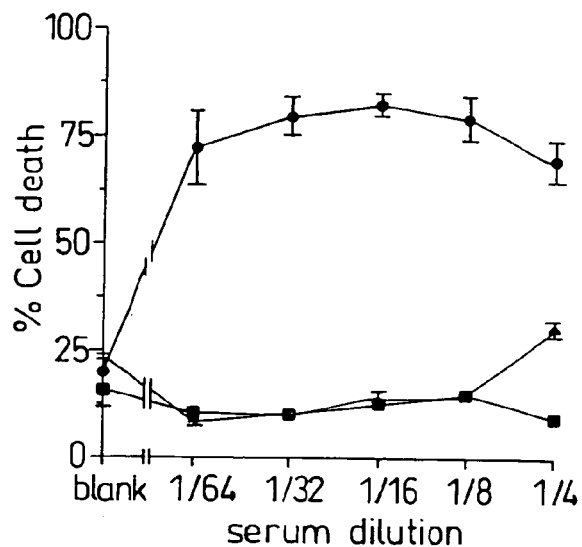

a: K562 cells were growth-arrested either by nutrient deprivation (triangles) or by maintaining at confluence in culture (squares). Control cells (circles) had been maintained in log growth in normal medium. Cells were then antibody sensitised and exposed to various dilutions of human serum. End-point lysis was measured at 60 min.
b: Cells growth arrest as above were stained for the various complement inhibitors and analysed on the FACScan. Open bar; control; hatched bar; confluence; solid bar; nutrient deprived. All points are mean +/- SD of triplicates.

*Fig. 21a*

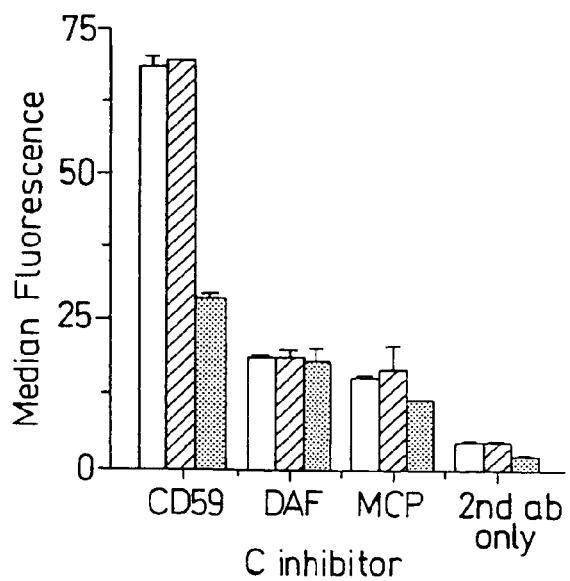

*Fig 21b*

Expression of pig CD59 on pig aortic endothelial cells (PAEC) at different passages.

Cells were harvested from pig aortae and cultured. Cells were stained for pig CD59 using mAb's Mel2 and Mel3. after 1 day culturing (Primary) or after subculturing (P1-P5, appr. 4-7 days between passages).

Expression of pig MCP on pig aortic endothelial cells (PAEC) at different passages.

Cells were harvested from pig aortae and cultured. Cells were stained for pig CD59 using mAb's 4C8 and 1C5. after 1 day culturing (Primary) or after subculturing (P1-P5, appr. 7 days between passages).

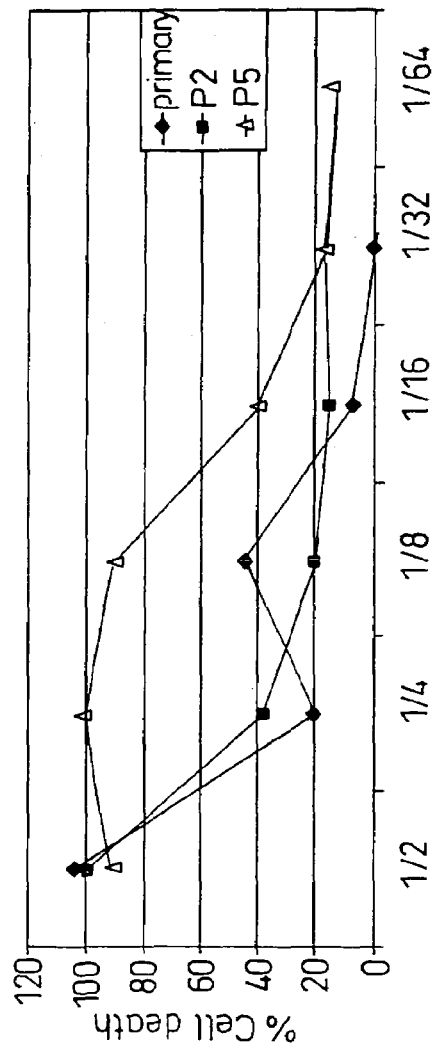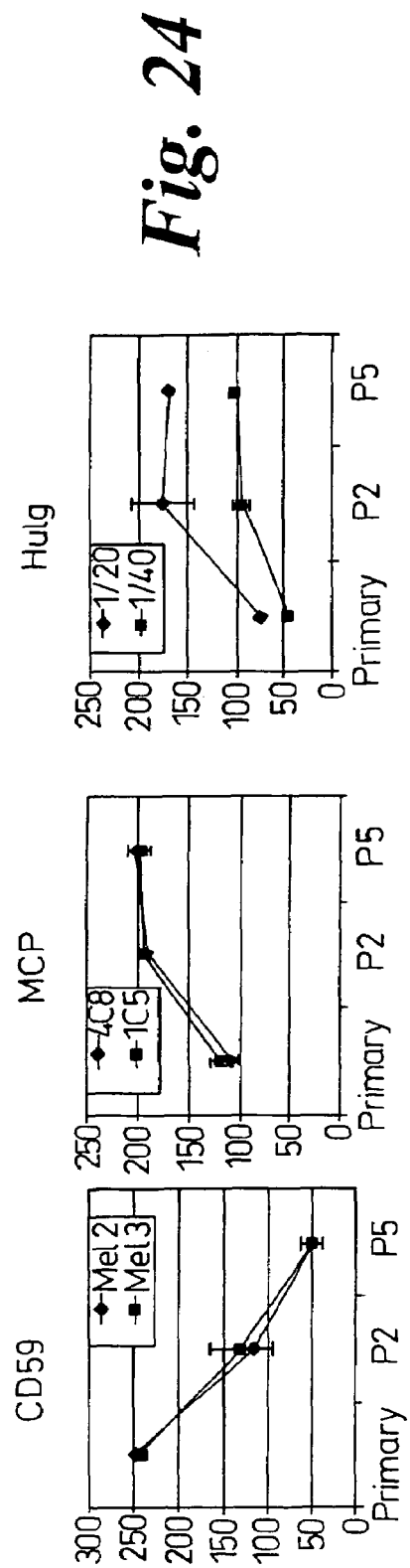
Fig. 24

Incorporation of Human CD59 into PAEC and effect of blocking of human and pig CD59 on C-susceptibility.

PAEC were incubated with 1 µg/ml CD59 for 30 min and followed by incubation with blocking antibodies against Human CD59 (Bric229) and pig CD59 (Mel2). Cells were assayed for C-susceptibility and levels of pig and human CD59

SEQUENCE LISTING

```
<160> NUMBER OF SEQ ID NOS: 24

<210> SEQ ID NO 1
<211> LENGTH: 123
<212> TYPE: PRT
<213> ORGANISM: Porcus sp.

<400> SEQUENCE: 1

Met Gly Ser Lys Gly Gly Phe Ile Leu Leu Trp Leu Leu Ser Ile Leu
 1               5                  10                  15

Ala Val Leu Cys His Leu Gly His Ser Leu Gln Cys Tyr Asn Cys Ile
                20                  25                  30

Asn Pro Ala Gly Ser Cys Thr Thr Ala Met Asn Cys Ser His Asn Gln
            35                  40                  45

Asp Ala Cys Ile Phe Val Glu Ala Val Pro Pro Lys Thr Tyr Tyr Gln
        50                  55                  60

Cys Trp Arg Phe Asp Glu Cys Asn Phe Asp Phe Ile Ser Arg Asn Leu
    65                  70                  75                  80

Ala Glu Lys Lys Leu Lys Tyr Asn Cys Cys Arg Lys Asp Leu Cys Asn
                85                  90                  95

Lys Ser Asp Ala Thr Ile Ser Ser Gly Lys Thr Ala Leu Leu Val Ile
            100                 105                 110

Leu Leu Leu Val Ala Thr Trp His Phe Cys Leu
        115                 120

<210> SEQ ID NO 2
<211> LENGTH: 773
<212> TYPE: DNA
<213> ORGANISM: Porcus sp.
<220> FEATURE:
```

```
<221> NAME/KEY: CDS
<222> LOCATION: (90)..(458)

<400> SEQUENCE: 2
gaaaagacgc gcaggccggg ccgctctccc gacggggagt agcgctgcag ccggacgcag      60
ggtgcagtta gaatccatag acggtcacg atg gga agc aaa gga ggg ttc att      113
                                 Met Gly Ser Lys Gly Gly Phe Ile
                                  1               5 ttg ctc tgg ctc ctg tcc atc ctg gct gtt ctc tgc cac tta ggt cac      161
Leu Leu Trp Leu Leu Ser Ile Leu Ala Val Leu Cys His Leu Gly His
 10              15                  20 agc ctg cag tgc tat aac tgt atc aac cca gct ggt agc tgc act acg      209
Ser Leu Gln Cys Tyr Asn Cys Ile Asn Pro Ala Gly Ser Cys Thr Thr
 25              30                  35                  40 gcc atg aat tgt tca cat aat cag gat gcc tgt atc ttc gtt gaa gcc      257
Ala Met Asn Cys Ser His Asn Gln Asp Ala Cys Ile Phe Val Glu Ala
                 45                  50                  55 gtg cca ccc aaa act tac tac cag tgt tgg agg ttc gat gaa tgc aat      305
Val Pro Pro Lys Thr Tyr Tyr Gln Cys Trp Arg Phe Asp Glu Cys Asn
                 60                  65                  70 ttc gat ttc att tcg aga aac cta gcg gag aag aag ctg aag tac aac      353
Phe Asp Phe Ile Ser Arg Asn Leu Ala Glu Lys Lys Leu Lys Tyr Asn
             75                  80                  85 tgc tgc cgg aag gac ctg tgt aac aag agt gat gcc acg att tca tca      401
Cys Cys Arg Lys Asp Leu Cys Asn Lys Ser Asp Ala Thr Ile Ser Ser
 90                  95                 100 ggg aaa acc gct ctg ctg gtg atc ctg ctg ctg gta gca acc tgg cac      449
Gly Lys Thr Ala Leu Leu Val Ile Leu Leu Leu Val Ala Thr Trp His
105                 110                 115                 120 ttt tgt ctc taactgtaca ccaggagagt ttctcctcaa cttcctctgt               498
Phe Cys Leu ctctctgttc ctatttccca tgctgcggtg ttccaaaggc tgtgtatgct ccagcttctt     558
cctgttggga aggactaaac ctagcttgag cactttggat tagagagaga aactttgagc     618
gactttgaag accaggcctg ttggcagaga agacctgtca gaggggaaac gttttaagag     678
tgaagcacag gtgatttgag cgaggcctat gcgtcttcct ctgctcttgg caggaccagc     738
tttgcggtaa ccattcgata gattccacaa tcctt                                773

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 3
tgytayaayt gyathaa                                                    17

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 4
agrtcytyyt krcarca                                                    17

<210> SEQ ID NO 5
<211> LENGTH: 36
```

```
<212> TYPE: DNA
<213> ORGANISM: Artificial Sequence
<220> FEATURE:
<223> OTHER INFORMATION: Description of Artificial Sequence: Primer

<400> SEQUENCE: 5
ccagtgagca gagtgacgag gactcgagct caagct                          36

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 6
ccagtgagca gagtgacg                                              18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 7
gaggactcga gctcaagc                                              18

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
tgcactacgg ccatgaattg                                            20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 9
tcgttgaagc cgtgccaccc                                            20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 10
aggtccttct tgcagcagtg                                            20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
```
cttctccgct aggtttctcg                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 12
gcattcatcg aacctccaac                                              20

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 13
ggttctagag tagcgctgca gccggac                                      27

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 14
ggtggatcct tctctgccaa caggcct                                      27

<210> SEQ ID NO 15
<211> LENGTH: 1637
<212> TYPE: DNA
<213> ORGANISM: Porcus sp.
<220> FEATURE:
<221> NAME/KEY: modified_base
<222> LOCATION: (17)
<223> OTHER INFORMATION: a, t, c, g, other or unknown
<220> FEATURE:
<221> NAME/KEY: modified_base
<222> LOCATION: (1323)
<223> OTHER INFORMATION: a, t, c, g, other or unknown
<220> FEATURE:
<221> NAME/KEY: modified_base
<222> LOCATION: (1330)
<223> OTHER INFORMATION: a, t, c, g, other or unknown
<220> FEATURE:
<221> NAME/KEY: modified_base
<222> LOCATION: (1357)
<223> OTHER INFORMATION: a, t, c, g, other or unknown
<220> FEATURE:
<221> NAME/KEY: modified_base
<222> LOCATION: (1378)
<223> OTHER INFORMATION: a, t, c, g, other or unknown
<220> FEATURE:
<221> NAME/KEY: modified_base
<222> LOCATION: (1403)
<223> OTHER INFORMATION: a, t, c, g, other or unknown
<220> FEATURE:
<221> NAME/KEY: modified_base
<222> LOCATION: (1424)
<223> OTHER INFORMATION: a, t, c, g, other or unknown
<220> FEATURE:
<221> NAME/KEY: modified_base
<222> LOCATION: (1437)
<223> OTHER INFORMATION: a, t, c, g, other or unknown
<220> FEATURE:
<221> NAME/KEY: modified_base
<222> LOCATION: (1445)
<223> OTHER INFORMATION: a, t, c, g, other or unknown

```
<220> FEATURE:
<221> NAME/KEY: modified_base
<222> LOCATION: (1513)
<223> OTHER INFORMATION: a, t, c, g, other or unknown
<220> FEATURE:
<221> NAME/KEY: modified_base
<222> LOCATION: (1520)
<223> OTHER INFORMATION: a, t, c, g, other or unknown
<220> FEATURE:
<221> NAME/KEY: modified_base
<222> LOCATION: (1527)
<223> OTHER INFORMATION: a, t, c, g, other or unknown
<220> FEATURE:
<221> NAME/KEY: modified_base
<222> LOCATION: (1535)
<223> OTHER INFORMATION: a, t, c, g, other or unknown
<220> FEATURE:
<221> NAME/KEY: modified_base
<222> LOCATION: (1544)
<223> OTHER INFORMATION: a, t, c, g, other or unknown
<220> FEATURE:
<221> NAME/KEY: modified_base
<222> LOCATION: (1563)
<223> OTHER INFORMATION: a, t, c, g, other or unknown
<220> FEATURE:
<221> NAME/KEY: modified_base
<222> LOCATION: (1588)
<223> OTHER INFORMATION: a, t, c, g, other or unknown
<220> FEATURE:
<221> NAME/KEY: modified_base
<222> LOCATION: (1609)..(1611)
<223> OTHER INFORMATION: a, t, c, g, other or unknown
<220> FEATURE:
<221> NAME/KEY: modified_base
<222> LOCATION: (1625)
<223> OTHER INFORMATION: a, t, c, g, other or unknown

<400> SEQUENCE: 15
ccaccgcggt ggcggcncgc tctagaacta gtggatcccc cgggctgcag gaattcggca      60
cgagatttcg tcttaatcgc ggaggtcgca gagtccggga gccgctcggg gtccccgttc     120
ccgcgcgcca tgagtcccct gccgcggagc gcccccgcgg tgaggcgcct aatgggcgga     180
cagacgccgc cgccgctgct gctgctgctg ctgctgctgt gtatcccggc tgcgcagggt     240
gactgcagcc ttccacccga tgtacctaat gcccaaccag atttgcgagg tcttgcaagt     300
tttcctgaac aaaccacaat aacatacaaa tgtaacaaag ctttgtcaa agttcctggc      360 atggcagact cagtgctctg tcttaatgat aaatggtcag aagttgcaga attttgtaat     420
cgtagctgtg atgttccaac caggctacat tttgcatctc ttaaaaagtc ttacagcaaa     480
cagaattatt tcccagaggg tttcaccgtg gaatatgagt gccgtaaggg ctataaaagg     540
gatcttactc tatcagaaaa actaacttgc cttcagaatt ttacgtggtc caaacctgat     600
gaattttgca aaaaaaaaca atgtccgact cctggagaac taaaaaatgg tcatgtcaat     660
ataacaactg acttgttatt tggcgcatcc atcttttct catgtaacgc agggtacaga     720
ctagttggtg caacttctag ttactgtttt gccatagcaa atgatgttga gtggagtgat     780
ccattgccag attgccaaga aatttctcca actgtcaaag ccataccagc tgttgagaaa     840
cccatcacag taaattttcc agcaacaaag tatccagcta ttcccagggc cacaacgagt     900
tttcattcaa gtacatctaa aaatcgagga aaccttctt caggcatgag aatcatgtcg     960
tctggtacca tgctacttat tgcaggaggt gttgctgtta ttataataat tgttgcccta    1020
attctagcca aaggtttctg gcactatgga aaatcaggct cttaccacac tcatgagaac    1080
aacaaagccg ttaatgttgc atttttataat ttacctgcga ctggcgatgc cgcagatgta    1140
agacctggta attaacaaaa ggacgtgcat gtgtaacact gacagttttg cttatggtgc    1200
```

-continued

```
tagtaaccat tggctagctg acttagccaa agaagagtta agaagaaagt gcacacaagt    1260
acacagaata ttttcagttt cttaaaactt tcaggtggga gtggacatag tttgtggtag    1320
tgntcttcgn tttgcatggt ttcattggct ctaaggnaca taggaatgca cagaaccnaa    1380
gagaaacaaa tctatcctga aantacatcc tcaacacttc taanactctt ggaaatngaa    1440
caagntcata agattgggag caattacttt cccaaaaggg tgagaaaaat ggagaaattt    1500
ggtcatgggt agnaattttn gaaaaangaa acccnaaagg gganttttcc cccccaaagg    1560
ggnaagggta tttttattta attaaggnaa aaaaaaaaa aaaaaccenn nggggggggcc    1620 cgggncccat tttccct                                                   1637
```

<210> SEQ ID NO 16
<211> LENGTH: 978
<212> TYPE: DNA
<213> ORGANISM: Porcus sp.

<400> SEQUENCE: 16

```
cacgagccgc cgccgctgct gctgctgctg ctgctgctgt gtatcccggc tgcgcagggt      60
gactgcagcc ttccacccga tgtacctaat gcccaaccag atttgcgagg tcttgcaagt     120
tttcctgaac aaaccacaat aacatacaaa tgtaacaaag gctttgtcaa agttcctggc     180
atggcagact cagtgctctg tcttaatgat aaatggtcag aagttgcaga attttgtaat     240
cgtagctgtg atgttccaac caggctacat tttgcatctc ttaaaaagtc ttacagcaaa     300
cagaattatt cccagagggt ttcaccgtg aatatgagt gccgtaaggg ctataaaagg       360
gatcttactc tatcagaaaa actaacttgc cttcagaatt ttacgtggtc caaacctgat     420
gaattttgca aaaaaaaaca atgtccgact cctggagaac taaaaaatgg tcatgtcaat     480
ataacaactg acttgttatt tggcgcatcc atcttttct catgtaacgc agggtacaga     540
ctagttggtg caacttctag ttactgtttt gccatagcaa atgatgttga gtggagtgat     600
ccattgccag aatgccaaga aatttctcca actgtcaaag ccataccagc tgttgagaaa     660
cccatcacag taaattttcc aggtaccaaa gccctatcat ctcctcagaa accctccaca     720
gcaaatactc tagctacaga gttactacca actcctcagg aacccaccac agtaaatgtt     780
ccagatagta agccatatc atctcctcag aaaccctcca cagtaaatac tccagctaca     840
gacttactac caactcctca ggaacccacc acagtaaatg ttccagatag taaagccata     900
tcatcttctc agaaaccctc cacagtaaat actccagctc agacttacta ccaactcctc     960
aggaacccac cacagtaa                                                   978
```

<210> SEQ ID NO 17
<211> LENGTH: 327
<212> TYPE: PRT
<213> ORGANISM: Porcus sp.
<220> FEATURE:
<221> NAME/KEY: MOD_RES
<222> LOCATION: (322)
<223> OTHER INFORMATION: Any amino acid

<400> SEQUENCE: 17

Met Gly Gly Gln Thr Pro Pro Leu Leu Leu Leu Leu Leu Leu
 1               5                  10                  15

Cys Ile Pro Ala Ala Gln Gly Asp Cys Ser Leu Pro Pro Asp Val Pro
             20                  25                  30

Asn Ala Gln Pro Asp Leu Arg Gly Leu Ala Ser Phe Pro Glu Gln Thr
         35                  40                  45

```
Thr Ile Thr Tyr Lys Cys Asn Lys Gly Phe Val Lys Val Pro Gly Met
 50                  55                  60

Ala Asp Ser Val Leu Cys Leu Asn Asp Lys Trp Ser Glu Val Ala Glu
 65                  70                  75                  80

Phe Cys Asn Arg Ser Cys Asp Val Pro Thr Arg Leu His Phe Ala Ser
                 85                  90                  95

Leu Lys Lys Ser Tyr Ser Lys Gln Asn Tyr Phe Pro Glu Gly Phe Thr
                100                 105                 110

Val Glu Tyr Glu Cys Arg Lys Gly Tyr Lys Arg Asp Leu Thr Leu Ser
            115                 120                 125

Glu Lys Leu Thr Cys Leu Gln Asn Phe Thr Trp Ser Lys Pro Asp Glu
130                 135                 140

Phe Cys Lys Lys Gln Cys Pro Thr Pro Gly Glu Leu Lys Asn Gly
145                 150                 155                 160

His Val Asn Ile Thr Thr Asp Leu Leu Phe Gly Ala Ser Ile Phe Phe
                165                 170                 175

Ser Cys Asn Ala Gly Tyr Arg Leu Val Gly Ala Thr Ser Ser Tyr Cys
                180                 185                 190

Phe Ala Ile Ala Asn Asp Val Glu Trp Ser Asp Pro Leu Pro Asp Cys
                195                 200                 205

Gln Glu Ile Ser Pro Thr Val Lys Ala Ile Pro Ala Val Glu Lys Pro
210                 215                 220

Ile Thr Val Asn Phe Pro Ala Thr Lys Tyr Pro Ala Ile Pro Arg Ala
225                 230                 235                 240

Thr Thr Ser Phe His Ser Ser Thr Ser Lys Asn Arg Gly Asn Pro Ser
                245                 250                 255

Ser Gly Met Arg Ile Met Ser Ser Gly Thr Met Leu Leu Ile Ala Gly
                260                 265                 270

Gly Val Ala Val Ile Ile Ile Val Ala Leu Ile Leu Ala Lys Gly
            275                 280                 285

Phe Trp His Tyr Gly Lys Ser Gly Ser Tyr His Thr His Glu Asn Asn
290                 295                 300

Lys Ala Val Asn Val Ala Phe Tyr Asn Leu Pro Ala Thr Gly Asp Ala
305                 310                 315                 320

Ala Xaa Val Arg Pro Gly Asn
                325

<210> SEQ ID NO 18
<211> LENGTH: 325
<212> TYPE: PRT
<213> ORGANISM: Porcus sp.

<400> SEQUENCE: 18

His Glu Pro Pro Leu Leu Leu Leu Leu Leu Leu Leu Cys Ile Pro
  1               5                  10                  15

Ala Ala Gln Gly Asp Cys Ser Leu Pro Pro Asp Val Pro Asn Ala Gln
                 20                  25                  30

Pro Asp Leu Arg Gly Leu Ala Ser Phe Pro Glu Gln Thr Thr Ile Thr
                 35                  40                  45

Tyr Lys Cys Asn Lys Gly Phe Val Lys Val Pro Gly Met Ala Asp Ser
 50                  55                  60

Val Leu Cys Leu Asn Asp Lys Trp Ser Glu Val Ala Glu Phe Cys Asn
 65                  70                  75                  80

Arg Ser Cys Asp Val Pro Thr Arg Leu His Phe Ala Ser Leu Lys Lys
                 85                  90                  95
```

```
Ser Tyr Ser Lys Gln Asn Tyr Phe Pro Glu Gly Phe Thr Val Glu Tyr
            100                 105                 110

Glu Cys Arg Lys Gly Tyr Lys Arg Asp Leu Thr Leu Ser Glu Lys Leu
            115                 120                 125

Thr Cys Leu Gln Asn Phe Thr Trp Ser Lys Pro Asp Glu Phe Cys Lys
            130                 135                 140

Lys Lys Gln Cys Pro Thr Pro Gly Glu Leu Lys Asn Gly His Val Asn
145                 150                 155                 160

Ile Thr Thr Asp Leu Leu Phe Gly Ala Ser Ile Phe Phe Ser Cys Asn
                165                 170                 175

Ala Gly Tyr Arg Leu Val Gly Ala Thr Ser Ser Tyr Cys Phe Ala Ile
            180                 185                 190

Ala Asn Asp Val Glu Trp Ser Asp Pro Leu Pro Glu Cys Gln Glu Ile
            195                 200                 205

Ser Pro Thr Val Lys Ala Ile Pro Ala Val Glu Lys Pro Ile Thr Val
            210                 215                 220

Asn Phe Pro Gly Thr Lys Ala Leu Ser Ser Pro Gln Lys Pro Ser Thr
225                 230                 235                 240

Ala Asn Thr Leu Ala Thr Glu Leu Leu Pro Thr Pro Gln Glu Pro Thr
                245                 250                 255

Thr Val Asn Val Pro Asp Ser Lys Ala Ile Ser Ser Pro Gln Lys Pro
            260                 265                 270

Ser Thr Val Asn Thr Pro Ala Thr Asp Leu Leu Pro Thr Pro Gln Glu
            275                 280                 285

Pro Thr Thr Val Asn Val Pro Asp Ser Lys Ala Ile Ser Ser Ser Gln
            290                 295                 300

Lys Pro Ser Thr Val Asn Thr Pro Ala Gln Thr Tyr Tyr Gln Leu Leu
305                 310                 315                 320

Arg Asn Pro Pro Gln
                325

<210> SEQ ID NO 19
<211> LENGTH: 376
<212> TYPE: PRT
<213> ORGANISM: Homo sapiens

<400> SEQUENCE: 19

Pro Ser Val Pro Ala Ala Leu Pro Leu Leu Gly Glu Leu Pro Arg Leu
1               5                   10                  15

Leu Leu Leu Val Leu Leu Cys Leu Pro Ala Val Trp Gly Asp Cys Gly
            20                  25                  30

Leu Pro Pro Asp Val Pro Asn Ala Gln Pro Ala Leu Glu Gly Arg Thr
            35                  40                  45

Ser Phe Pro Glu Asp Thr Val Ile Thr Tyr Lys Cys Glu Glu Ser Phe
        50                  55                  60

Val Lys Ile Pro Gly Glu Lys Asp Ser Val Thr Cys Leu Lys Gly Met
65                  70                  75                  80

Gln Trp Ser Asp Ile Glu Glu Phe Cys Asn Arg Ser Cys Glu Val Pro
                85                  90                  95

Thr Arg Leu Asn Ser Ala Ser Leu Lys Gln Pro Tyr Ile Thr Gln Asn
            100                 105                 110

Tyr Phe Pro Val Gly Thr Val Val Glu Tyr Glu Cys Arg Pro Gly Tyr
            115                 120                 125

Arg Arg Glu Pro Ser Leu Ser Pro Lys Leu Thr Cys Leu Gln Asn Leu
```

```
                130                 135                 140
Lys Trp Ser Thr Ala Val Glu Phe Cys Lys Lys Ser Cys Pro Asn
145                 150                 155                 160

Pro Gly Glu Ile Arg Asn Gly Gln Ile Asp Val Pro Gly Gly Ile Leu
                165                 170                 175

Phe Gly Ala Thr Ile Ser Phe Ser Cys Asn Thr Gly Tyr Lys Leu Phe
                180                 185                 190

Gly Ser Thr Ser Ser Phe Cys Leu Ile Ser Gly Ser Ser Val Gln Trp
                195                 200                 205

Ser Asp Pro Leu Pro Glu Cys Arg Glu Ile Tyr Cys Pro Ala Pro Pro
210                 215                 220

Gln Ile Asp Asn Gly Ile Ile Gln Gly Glu Arg Asp His Tyr Gly Tyr
225                 230                 235                 240

Arg Gln Ser Val Thr Tyr Ala Cys Asn Lys Gly Phe Thr Met Ile Gly
                245                 250                 255

Glu His Ser Ile Tyr Cys Thr Val Asn Asn Asp Glu Gly Glu Trp Ser
                260                 265                 270

Gly Pro Pro Pro Glu Cys Arg Gly Lys Ser Leu Thr Ser Lys Val Pro
                275                 280                 285

Pro Thr Val Gln Lys Pro Thr Thr Val Asn Val Pro Thr Thr Glu Val
290                 295                 300

Ser Pro Thr Ser Gln Lys Thr Thr Thr Lys Thr Thr Thr Pro Asn Ala
305                 310                 315                 320

Gln Ala Thr Arg Ser Thr Pro Val Ser Arg Thr Thr Lys His Phe His
                325                 330                 335

Glu Thr Thr Pro Asn Lys Gly Ser Gly Thr Thr Ser Gly Thr Thr Arg
                340                 345                 350

Leu Leu Ser Gly His Thr Cys Phe Thr Leu Thr Gly Leu Leu Gly Thr
                355                 360                 365

Leu Val Thr Met Gly Leu Leu Thr
                370                 375

<210> SEQ ID NO 20
<211> LENGTH: 128
<212> TYPE: PRT
<213> ORGANISM: Homo sapiens

<400> SEQUENCE: 20

Met Gly Ile Gln Gly Gly Ser Val Leu Phe Gly Leu Leu Leu Val Leu
1               5                   10                  15

Ala Val Phe Cys His Ser Gly His Ser Leu Gln Cys Tyr Asn Cys Pro
                20                  25                  30

Asn Pro Thr Ala Asp Cys Lys Thr Ala Val Asn Cys Ser Ser Asp Phe
                35                  40                  45

Asp Ala Cys Leu Ile Thr Lys Ala Gly Leu Gln Val Tyr Asn Lys Cys
        50                  55                  60

Trp Lys Phe Glu His Cys Asn Phe Asn Asp Val Thr Thr Arg Leu Arg
65                  70                  75                  80

Glu Asn Glu Leu Thr Tyr Tyr Cys Cys Lys Lys Asp Leu Cys Asn Phe
                85                  90                  95

Asn Glu Gln Leu Glu Asn Gly Gly Thr Ser Leu Ser Glu Lys Thr Val
                100                 105                 110

Leu Leu Leu Val Thr Pro Phe Leu Ala Ala Ala Trp Ser Leu His Pro
                115                 120                 125
```

```
<210> SEQ ID NO 21
<211> LENGTH: 126
<212> TYPE: PRT
<213> ORGANISM: Rattus sp.

<400> SEQUENCE: 21

Met Arg Ala Arg Arg Gly Phe Ile Leu Leu Leu Leu Ala Val Leu
 1               5                  10                  15

Cys Ser Thr Gly Val Ser Leu Arg Cys Tyr Asn Cys Leu Asp Pro Val
                20                  25                  30

Ser Ser Cys Lys Thr Asn Ser Thr Cys Ser Pro Asn Leu Asp Ala Cys
            35                  40                  45

Leu Val Ala Val Ser Gly Lys Gln Val Tyr Gln Gln Cys Trp Arg Phe
    50                  55                  60

Ser Asp Cys Asn Ala Lys Phe Ile Leu Ser Arg Leu Glu Ile Ala Asn
65                  70                  75                  80

Val Gln Tyr Arg Cys Cys Gln Ala Asp Leu Cys Asn Lys Ser Phe Glu
                85                  90                  95

Asp Lys Pro Asn Asn Gly Ala Ile Ser Leu Leu Gly Lys Thr Ala Leu
            100                 105                 110

Leu Val Thr Ser Val Leu Ala Ala Ile Leu Lys Pro Cys Phe
        115                 120                 125

<210> SEQ ID NO 22
<211> LENGTH: 123
<212> TYPE: PRT
<213> ORGANISM: Murine sp.

<400> SEQUENCE: 22

Met Arg Ala Gln Arg Gly Leu Ile Leu Leu Leu Leu Leu Ala Val
 1               5                  10                  15

Phe Cys Ser Thr Ala Val Ser Leu Thr Cys Tyr His Cys Phe Gln Pro
                20                  25                  30

Val Val Ser Ser Cys Asn Met Asn Ser Thr Cys Ser Pro Asp Gln Asp
            35                  40                  45

Ser Cys Leu Tyr Ala Val Ala Gly Met Gln Val Tyr Gln Arg Cys Trp
    50                  55                  60

Lys Gln Ser Asp Cys His Gly Glu Ile Ile Met Asp Gln Leu Glu Glu
65                  70                  75                  80

Thr Lys Leu Lys Phe Arg Cys Cys Gln Phe Asn Leu Cys Asn Lys Ser
                85                  90                  95

Asp Gly Ser Leu Gly Lys Thr Pro Leu Leu Gly Thr Ser Val Leu Val
            100                 105                 110

Ala Ile Leu Asn Leu Cys Phe Leu Ser His Leu
        115                 120

<210> SEQ ID NO 23
<211> LENGTH: 6
<212> TYPE: PRT
<213> ORGANISM: Homo sapiens

<400> SEQUENCE: 23

Cys Cys Lys Lys Asp Leu
 1               5

<210> SEQ ID NO 24
<211> LENGTH: 14
<212> TYPE: PRT
```

-continued

```
<213> ORGANISM: Artificial Sequence
<220> FEATURE:
<223> OTHER INFORMATION: Description of Artificial Sequence:
      Illustrative peptide
<220> FEATURE:
<221> NAME/KEY: MOD_RES
<222> LOCATION: (7)
<223> OTHER INFORMATION: Any amino acid
<220> FEATURE:
<221> NAME/KEY: MOD_RES
<222> LOCATION: (10)
<223> OTHER INFORMATION: Any amino acid

<400> SEQUENCE: 24

Asp Cys Gly Leu Pro Pro Xaa Val Pro Xaa Ala Gln Pro Ala
 1               5                  10
```

PORCINE CD59 NUCLEIC ACIDS AND CELLS CONTAINING THE SAME

CROSS REFERENCE TO RELATED APPLICATIONS

This application is a division of co-pending application Ser. No. 09/673,032, filed on Dec. 6, 2000, application Ser. No. 09/673,032 is the national phase of PCT International Application No. PCT/GB99/01085 filed on Apr. 8, 1999 under 35 U.S.C. §371. The entire contents of each of the above-identified applications are hereby incorporated by reference.

This invention relates to modified biological materials and their use in transplants and also to associated methods. In particular, but not exclusively, the invention relates to the enhanced expression of endogenous complement regulatory molecules as a strategy for protection of xenotransplants.

Host cells are protected from their own complement by membrane-bound complement regulatory proteins. In humans, decay-accelerating factor (DAP or CD55), membrane cofactor protein (MCP or CD46) and CD59 perform this function. When an organ is transplanted into another species, natural antibodies in the recipient bind the endothelium of the donor organ and activate complement, thereby initiating rapid rejection. The hyperacute rejection caused by preformed antibodies-and complement is a major barrier to the transplantation of pig organs to humans. It has previously been suggested that, in contrast to human cells, those of the pig are very susceptible to human complement, and it was thought that this was because pig cell-surface complement regulatory proteins are ineffective against human complement. When an organ is transplanted into another species, natural antibodies in the recipient bind the endothelium of the donor organ and activate complement, thereby initiating rapid rejection. In pig-to-primate transplants, most of the natural antibodies are Igm antibodies against the α-galactosyl epitope, which is expressed on pig endothelium but is absent in humans and primates. Several strategies have been shown to prevent or delay rejection, including removal of IgM natural antibodies and systemic decomplementation or inhibition of complement using sCR1, heparin or C1 inhibitor.

An alternative approach to the problem of hyperacute rejection is to express human, membrane-bound, complement-regulatory molecules in transgenic pigs. Transgenic pigs expressing DAF, MCP and CD59 have been generated, and these human inhibitors have been shown to be abundantly expressed on porcine vascular endothelium. Ex vivo perfusion of hearts from control animals with human blood caused complement-mediated destruction of the organ within minutes, whereas hearts obtained from transgenic animals were refactory to complement and survived for hours.

The rationale for expressing human complement regulatory proteins in pig organs to "humanise" them as outlined above is based on the assumption that endogenous pig regulatory proteins are inefficient at inhibiting human complement and thus will contribute little to organ survival in the context of xenotransplantation. Indeed, pig organs hyper-expressing human complement regulatory protein are much less susceptible to complement damage when perfused with human serum. However, it is our belief, based on experimental evidence, that the above assumption is incorrect.

It has been suggested that hyperacute rejection of xenotransplanted organs might be inhibited by hyperexpression of either pig or human CD59 in the organ (see van den Berg & Morgan,. J. Immuno., 152, 4095-4101 (1994)). However, until the present invention hyperexpression of pig CD59 was not possible. Even with the cloning of pig CD59 now available as presented here, it could not be-predicted that any expressed protein would function to inhibit human complement in nucleated porcine cells.

We have isolated and characterised the porcine analogues of several of the human complement regulatory proteins (CRP).

Porcine CD59 purified from pig erythrocytes inhibits human complement efficiently. We have cloned this molecule and shown that porcine CD59 expressed in a variety of cells is able efficiently to inhibit human complement.

Porcine MCP was purified from pig erythrocytes and has also been shown to inhibit human complement. We have recently demonstrated that neither of these porcine CRPs are species selective, and each inhibits both human and porcine complement to a similar degree.

We have also characterised another pig complement regulatory protein, porcine decay accelerating factor (DAP). This molecule has also been cloned and sequenced Our studies indicate that pig organs expressing human complement regulatory protein molecules are resistant to complement damage not because they express human CRP molecules, but because they express greatly increased amounts of functional CRP molecules. We have found unexpectedly that increased expression of porcine CRP can be equally effective in protecting the donor organ from complement damage leading to hyperacute rejection as donor organs expressing human complement regulatory proteins.

Thus the invention is based on the concept of manipulating endogenous CRP and other complement control mechanisms in porcine cells to generate organs, tissue and cells resistant to complement attack and hence to hyperacute rejection when transplanted into humans.

References herein to increased expression, hyper-expression, upregulated expression, etc., are used to mean that the cells are caused to express supra-physiological quantities of complement regulatory molecules. Although the extent of hyper-expression has not yet been fully established, our initial studies suggest that it should be several times that of the normal physiological level of expression, and possibly up to 10 times.

SUMMARY OF THE INVENTION

In one aspect, this invention provides a graftable animal cell or tissue of a donor species for use in medicine, wherein said cell or tissue expresses, or is capable of being caused to express, increased amounts of endogenous complement regulatory molecules for preventing activation of complement in a recipient species.

The cell or tissue is preferably for use in transplantation therapy, and may be an organ e.g. a heart, lung, liver, kidney, pancreas, or thyroid. The cells may be isolated cells, e.g. islet cells, neurones, stem cells. The tissue may be skin.

Preferably said complement regulatory molecules comprise complement regulatory proteins (CRPs).

The CRPs may comprise or have the activity of one or more, of CD59, Membrane Cofactor Protein (MCP; CD46), Decay Accelerating Factor (DAF;CD55); complement receptor 1 (CR1; CD35), homologous restriction factor (HRF).

The donor species may be any suitable species for harvesting the particular organ tissue required, given size etc. Thus, the donor species may be a pig or a sheep, or other species where appropriate. Likewise the recipient may be any suitable species requiring xenotransplantation, for example human.

In another aspect, this invention provides the use of an animal cell or tissue derived from a donor species, wherein one or more complement regulatory molecules endogenous to the donor species can be hyper-expressed to prevent complete activation of complement in a recipient species, in the preparation of tissue graftable into the recipient species without hyperacute rejection.

The invention also extends to a method of preparing an animal cell or tissue derived from a donor species for transplanting into a recipient species, and/or for reducing likelihood of hyperacute rejection once transplanted, which comprises causing said cell or tissue to express increased amounts of one or more endogenous complement regulatory molecules sufficient to prevent activation of complement in the recipient species.

Thus, for example the cell or tissue may be transfected with a viral vector encoding a complement regulatory molecule.

Alternatively, the method may comprise the use of cytokines or other factors acting directly or indirectly on regulatory elements in the CRP gene to increase expression of said CRP, before during or after transplant.

Cytokines are soluble proteins or glycoproteins produced by leukocytes and in some cases other cell types which act as chemical communicators between cells. Cytokines bind specific receptors on the surface of target cells which are coupled to intracellular signalling pathways. Preferred candidates for upregulation of CFP or other complement defence mechanisms on endothelia are the inflammatory cytokines tumor necrosis factor α (TNFα), interleukin-1β (IL-1β) and interferon-γ (IFN-γ). In the human, receptors for each of these cytokines are present on endothelia and each has been shown to increase adhesion molecule expression on endothelia. These molecules often work well across species barriers (that is, hyman cytokines will bind and activate cells from other species). Often, mixtures of several different cytokines have a much greater effect than the sum of the individual cytokines in activating target cells, and the invention extends to use of a combination thereof.

Chemokines are members of the cytokine superfamily distinguished by their ability to cause directed chemotaxis in some target cells. Receptors for several of these molecules and related chemoattractants such as the complement fragments C5a and C3a are known to be expressed on endothelia. The term cytokine is used broadly to include chemokines.

The invention also extends to a transgenic animal having cells or tissue which hyper-express endogenous complement regulatory proteins. It is preferred to provide a clone.

In yet another aspect of this invention, there is provided a method of increasing the resistance of an animal cell or tissue of a donor species to complement attack when transplanted into a recipient species, which comprises:
(a) exposing said cell or tissue to sub-lytic complement attack, or
(b) exposing the cell or tissue to nutrient deprivation or
(c) applying conditions of limited anoxia to the cell or tissue, or (d) exposing said cell or tissue to ionophores, or (e) exposing said cell or tissue exogenous chemicals such as lectins thereby to increase the resistance of said cell or tissue to complement attack.

Referring now to particular complement regulatory proteins, CD59 has been identified as an 18000-20000 MW glycosyl-phosphatidylinositol (GPI)-anchored protein that is a potent inhibitor of Complement attack during the formation of the membrane attack complex of complement (MAC). CD59 binds to C8 in the forming MAC, and limits incorporation of C9, thereby preventing the formation of a lytic lesion. Nucleated cells can also escape Complement killing by shedding vesicles enriched in the MAC and CD59. These recovery events are accompanied by increases in intra-cellular calcium concentration and other activation events, the triggers for which remain uncertain. Cross-linking of CD59 using monoclonal antibody (mAb) induces a cascade of events in nucleated cells that mimics non-lethal Complement attack and it has been proposed that non-lethal Complement attack may induce cell activation through interaction of CD59 with its natural ligand, the MAC. Therefore up-regulation of the Complement regulatory molecule CD59 during non-lethal Complement attack may be an important factor in rendering the cells less susceptible to subsequent Complement attack.

Analogues of human CD59 have been isolated by preparative SDS-PAGE; in particular, with respect to pig CD59, as described in J. Immunol. Meth. 179, 223-31 (1995). This method is based on the fractionation of a butanol extract of erythrocyte ghosts by preparative SDS-PAGE followed by gel filtration on Superose 12. Purification was monitored using a functional complement inhibition assay. SDS-PAGE analysis of the product of this procedure indicated a single protein band with apparent $M_r$ of 20 kDa under reducing and non-reducing conditions. The preparation could be incorporated into guinea pig E to inhibit both cobra venom factor-reactive lysis and lysis through C8 and C9 using preformed C5b-7 sites, demonstrating that it contained a CD59-like activity.

Despite the multi-stage purification procedure and apparent single band on SDS-PAGE, sequencing revealed two distinct signals at most cycles. Subtraction of the known sequence of the glycophorin fragment identified as a contaminant at the early stages of the preparation, beginning at residue 54 of the already published glycophorin sequence enabled the amino-terminal sequence of pig CD59 to be deduced. Repetitive yield plots for the two sequences were linear, providing good evidence for correct assignments. The amino acid terminal sequence published for the pig CD59 is given in SEQ ID NO:1 in which amino acid residues which were tentatively assigned as conserved cysteine or asparagine are shown in lower case.

We have now determined a full cDNA sequence for the pig CD59, cloned the molecule and also determined the functional characteristics of the expressed molecule.

Accordingly, in another aspect, this invention provides a DNA molecule selected from:
(a) a pig CD59 gene or its complementary strand;
(b) a sequence substantially homologous to, or capable of hybridising to, a substantial portion of the gene defined in (a) above;
(c) a mRNA coding for a polypeptide having an amino acid sequence defined in FIG. 2 (SEQ ID No. 2);
(d) genomic DNA corresponding to a molecule in (a) above, and
(e) a fragment of a molecule defined in any of (a), (b), (c), or (d) above, other than the fragment identified in SEQ ID No.1.

Since the pig CD59 gene encodes a protein called pCD59, the pig CD59 gene therefore includes the DNA sequence shown in FIG. 2 (SEQ ID No. 2), and all functional equivalents. The gene furthermore includes regulatory regions which control the expression of the pig CD59 coding sequence, including promoter, enhancer and terminator regions. Other DNA sequences such as introns spliced from the end-product pig CD59 RNA transcript are also encompassed.

Using probes prepared as a result of sequencing the amino terminal sequence of pig DAF, it has been possible to construct a pig testis cDNA library and subsequently to isolate clones encoding partial and full length pig DAF cDNA and thereafter to sequence pig DAF.

According to yet another aspect this invention provides DNA molecule selected from:
(a) a pig DAF gene or its complementary strand;
(b) a sequence substantially homologous to or capable of hybridising to, a substantial portion of a molecule defined in (a) above;
(c) a molecule coding for a polypeptide having the sequence of FIG. 15 (SEQ. ID. Nos 17-19);
(d) genomic DNA corresponding to a molecule in (a) above; and;
(e) a fragment of a molecule defined in any of (a), (b), (c), or (d) above The invention also extends to RNA molecules comprising an RNA sequence corresponding to any of the DNA sequences set out above.

In another aspect, the invention provides a nucleic acid probe having a sequence as set out above; in particular, this invention extends to a purified nucleic acid probe which hybridises to at least a portion of the DNA or RNA molecule of any of the preceding sequences. Preferably, the probe includes a suitable label such as a chemiluminescent label or a radiolabel.

One or more of the DNA molecules defined above may be incorporated in a recombinant cloning vector for expressing a protein(s) having the amino acid sequence of FIG. 2 and/or FIG. 15, or a protein or a polypeptide having at least one functional domain or active site in common with said protein.

In another aspect, the invention provides a polypeptide encoded by a sequence as set out above, or having the amino acid sequence according to the amino acid sequence of FIG. 2 (SEQ ID No. 2) or FIG. 15 (SEQ ID No. 15), a protein or polypeptide having homologous properties with said protein, or having at least one functional domain or active site in common with said protein.

In particular, there is provided an isolated, purified or recombinant polypeptide comprising a pCD59 protein or a pDAF protein or a mutant or variant thereof or encoded by a sequence set out above or a variant thereof having substantially the same activity as the pig CD59 protein or pig DAF protein.

The invention also extends to an anti-pig CD59 monoclonal antibody and to anti-pig DAF monclonal antibodies. We describe herein two such antibodies identified as MEL-1 and MEL-2 respectively.

Preferably the monoclonal antibodies have an associated label for use in observing, monitoring, purifying or localising pig CD59 or pig DAF in a sample.

LIST OF FIGURES

The present invention will now be further described with reference to the accompanying figures, in which:

FIG. 1 is a schematic diagram of the pig CD59 cDNA to show the position of primers used in degenerate PCR, 3' RACE, 5' RACE and in cloning the full length coding region. These primer positions are shown in relation to the 5'-untranslated region. (5' UTR), signal peptide, mature protein coding region, GPI-addition signal and 3'-untranslated region (3'-UTR).

FIG. 2 is the nucleotide (SEQ ID NO: 2) and deduced amino acid (SEQ ID NO: 1) sequence of pig CD59. The numbers below refer to the nucleotide sequence, the numbers on the right refer to the amino acid sequence. The first residue of the mature protein (L-1) is boxed. Potential N-glycosylation sites (N-X-S/T) are denoted by psi (Ψ). The arrow (⇓) indicates the putative GPI-anchor addition site (S-73). The pig CD59 GenBank accession number is AF020302.

FIG. 3 is the result of Northern blot analysis showing the relative expression of pig CD59 transcripts in different tissues detected using a cDNA radiolabelled probe derived from the coding region. A glyceraldehyde-3-phosphate dehydrogenase (GAPDH) probe was used as a control for loading of RNA between lanes. The lane marked "mRNA" contains mRNA isolated from cultured porcine endothelial cells. The positions of the major 1.3 kb and 1.8 kb transcripts are arrowed.

FIG. 4 is a comparison of pig CD59 protein sequence (SEQ ID NO: 1) with that of human (SEQ ID NO: 20), rat (SEQ ID NO: 21) and mouse (SEQ ID NO: 22) CD59. Numbering refers to the predicted pig CD59 sequence, with the first residue of the mature protein known from protein sequencing to be L. Vertical lines (|) show identity of conserved residues between pig CD59 and other species.

FIG. 5 represents expression of pig (A) and human (B) CD59 in the U937 cell line and effect of phosphatidylinositol-specific phospholipase C (PIPLC) treatment. Transfected U937 cells were incubated for 30 minutes at 37° C. with or without PIPLC (0.4U/ml). Appropriate cells were then stained with MEL-2 (anti-pig CD59) or BRIC229 (anti-human CD59) and analysed by flow cytometry. - - - binding of antibody to vector control cells; _(shaded), expression of CD59; _(non-shaded), PIPLC treated.

FIG. 6 shows the result of a Western blot of pig CD59 expressing U937 cells, vector transfected U937 cells and pig red blood cells (PRBC) run under non-reducing (NR) or reducing (Red) conditions using MEL-1 anti-pig CD59. Molecular weight markers are shown on the left. Identical results were obtained using a second anti-pig CD59 mAb (MEL2IgG1). Control blots with isotype-matched Ab showed no binding.

FIG. 7 relates to the classical pathway of complement mediated killing of U937 transfectants. Calcein-AM loaded cells were antibody sensitised and placed in 96-well plates. Cells were then incubated with varying dilutions of serum from several species. The species source is indicated in large letters at the top of each panel. Release of the fluorescent dye into the supernatant was measured on the WellFluor system and is expressed as a percentage of maximal release obtained after lysis of cells by detergent. ○, Vector; ■, Human CD59; ▲, Pig CD59; ◆, Pig CD59 with blocking antibody. Points are means of triplicates determinations +/− SDs.

FIG. 11 is a graph comparing the relative effectiveness of human sMCP and pig MCP as inhibitors of haemolysis by human serum;

Figure 12:
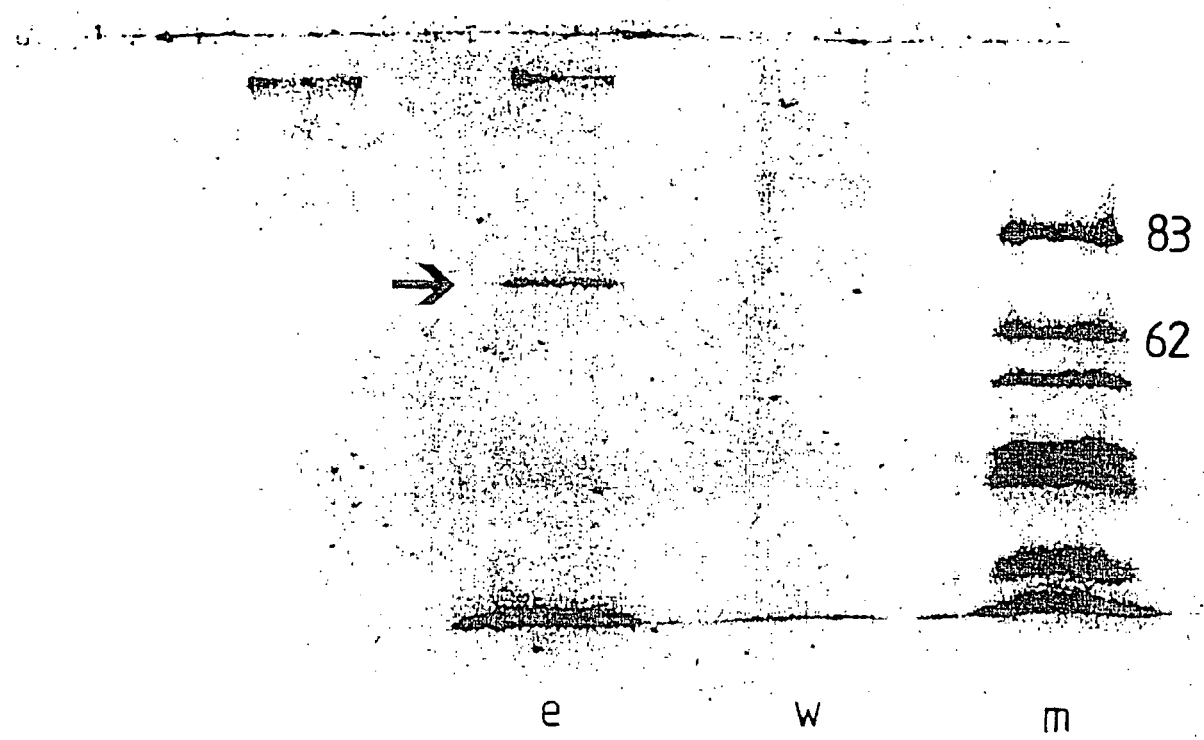

FIG. 12 is an SDS—PAGE gel of pig DAF illustrating presence of pig DAF with molecular weight of approximately 65 kDa. M=molecular weight markers; W=salt wash from column and e=column eluate with DAF band arrowed.

Figure 13:
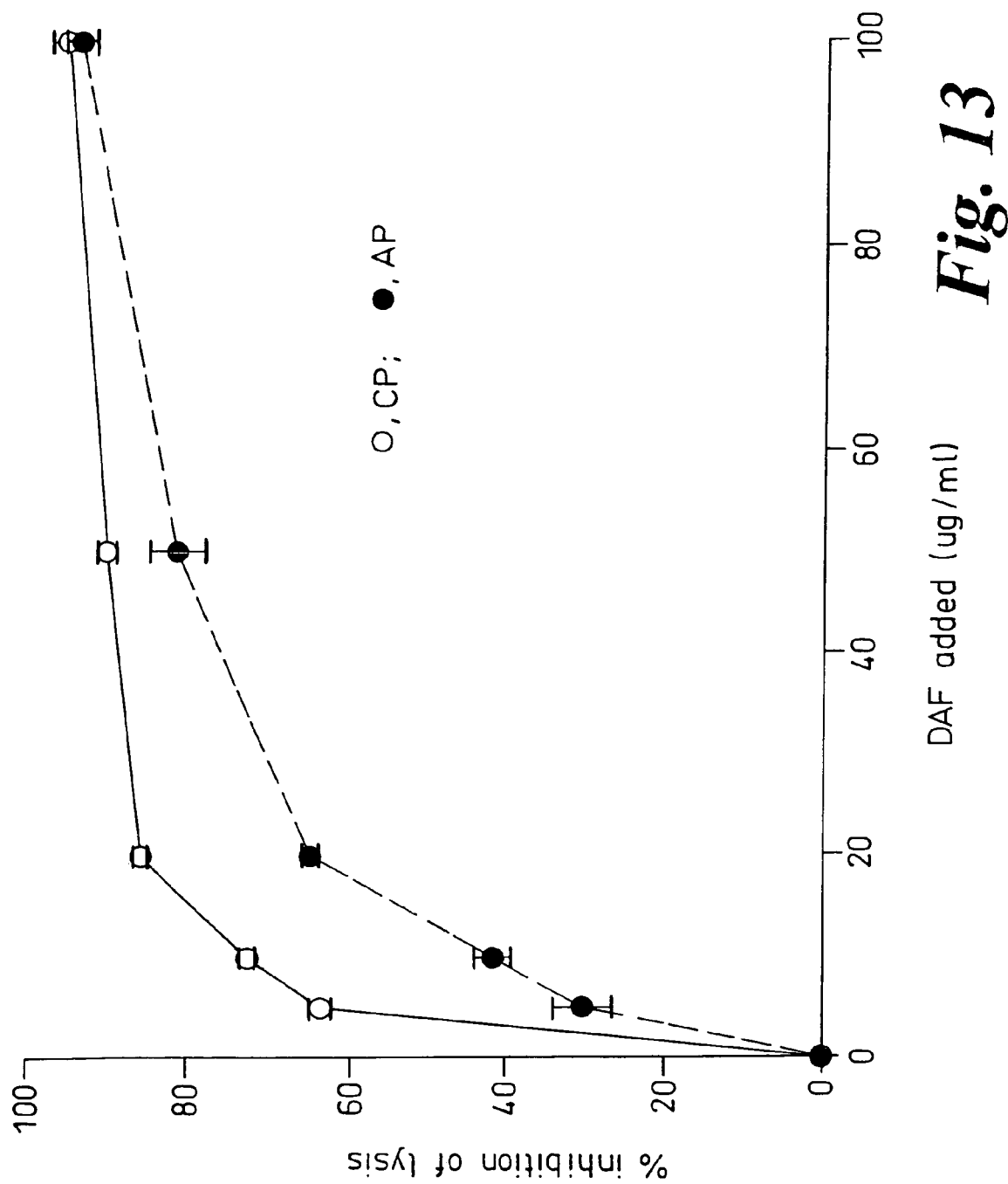

FIG. 13 is a graph illustrating the inhibition of lysis in guinea pig erythrocytes incorporating pig DAF.

FIG. 14 shows the nucleotide sequence of two different clones of pig DAF, i.e. pDAF-7 and pDAF-14 (SEQ ID Nos. 15 and 16). The pDAF-7 cDNA sequence corresponds to SEQ ID No. 15. The pDAF-4 cDNA sequence corresponds to SEQ ID No. 16.

FIG. 15 shows the predicted protein sequence of pig DAF from the nucleotide sequences of clones pDAF-7 and pDAF- 14 in FIG. 14. It also shows the alignment of the predicted protein sequence of clone pDAF-7 in alignment with the protein sequence of human DAF (SEQ ID Nos. 17, 18 and 19). The pDAF-7, predicted protein sequence corresponds to SEQ ID No. 17. The pDAF 14 predicted protein sequence corresponds to SEQ ID No. 18. The sequence shown in alignment with human DAF corresponds to SEQ ID No. 19.

Figure 16:
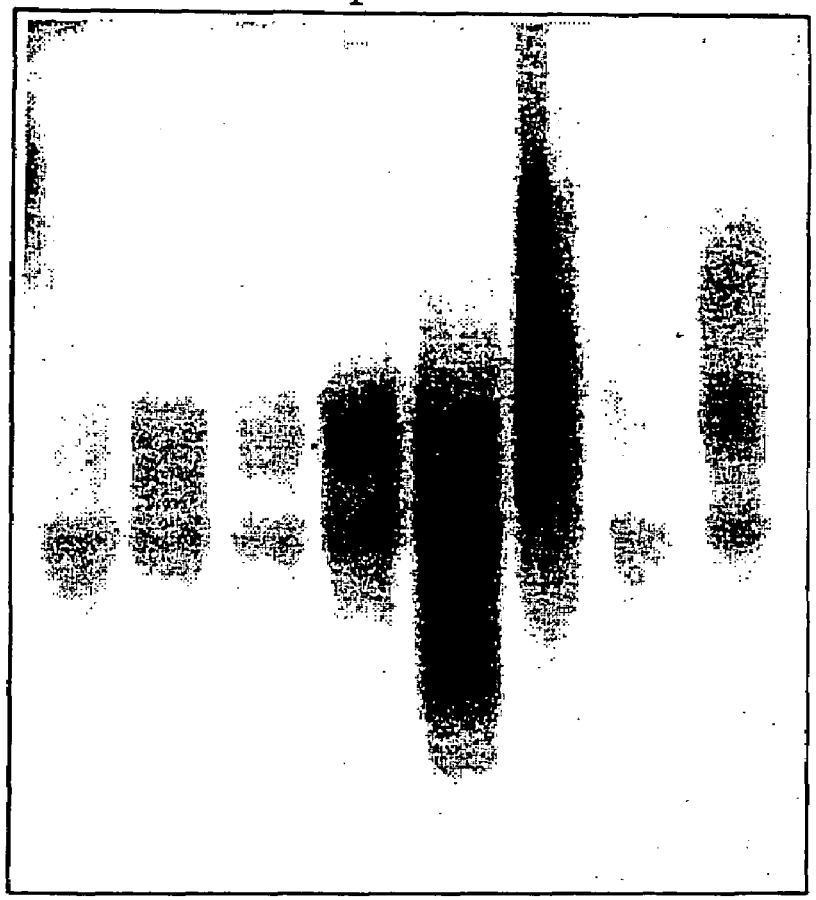

FIG. 16 is the result of Northern blot analysis showing the relative expression of pig DAF in different tissues detected using a cDNA probe derived from the pDAF sequence given in FIG. 14.

FIG. 17 shows the activity of a pig DAF-Fc fusion protein, purified from supernatants of transfected CHO cells by protein A chromatography, to inhibit pig and human complement a) Fixed dose of DAF-Fc, varying serum concentration; b) Fixed amount of serum, varying dose of DAF-Fc.

FIG. 18 contains two graphs showing the effect on complement susceptibility (a) and expression of CD59 and MCP (b) in primary pig aortic endothelial cells (PAEC) when treated with phorbol myristate acetate (PMA)

FIGS. 19a and 19b show the effect of exposure to non-lethal complement attack on the resistance to complement lysis of PAEC (a) or on the expression of CD59 and MCP (b) by the cells FIG. 20 shows the effect of anoxia on (a) susceptibility to complement lysis, and (b) expression of CD59 and MCP on PAEC FIGS. 21a and 21b show the effect of growth arrest induced by nutrient deprivation or cell density on the resistance to complement lysis of human erythroleukaemia cell line K562 and on the expression of CD59 and MCP by the cells.

Figure 22:
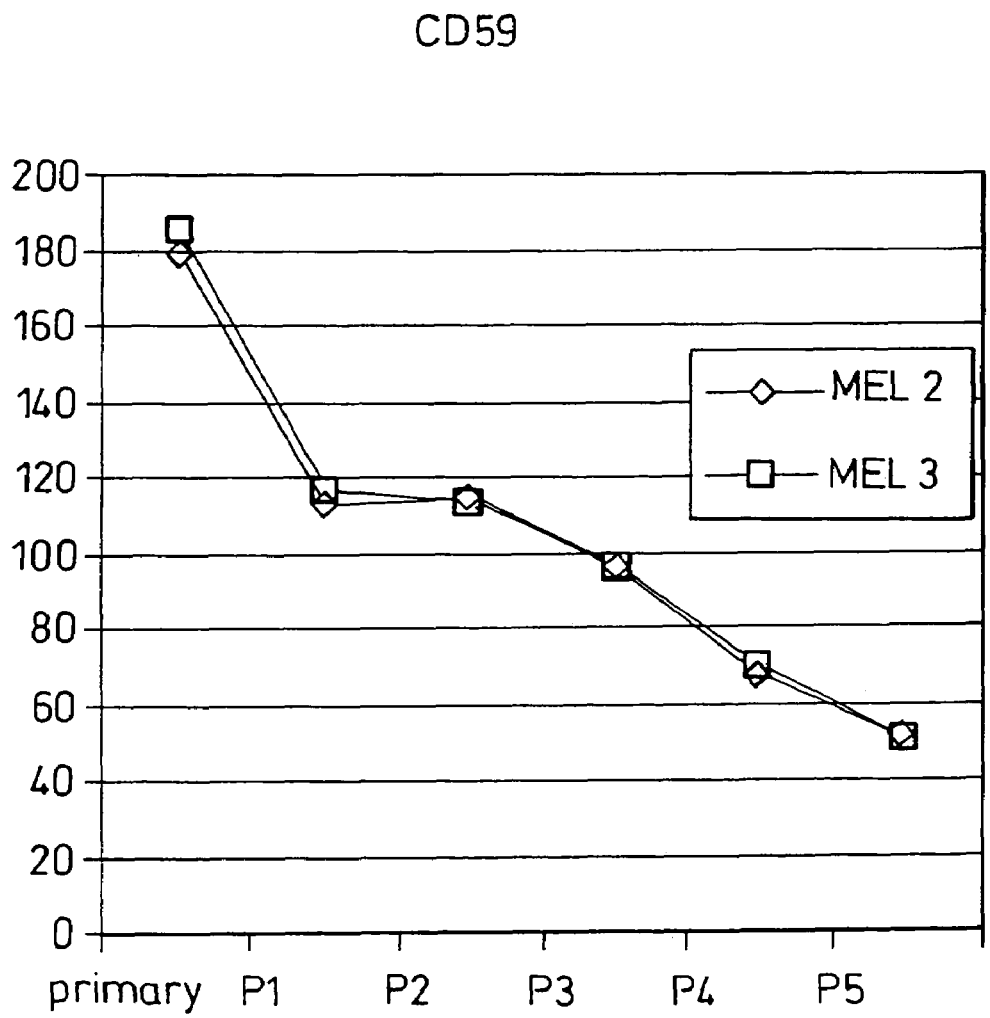

FIG. 22 shows the expression of pig CD59 on PAEC at different passages.

Figure 23:
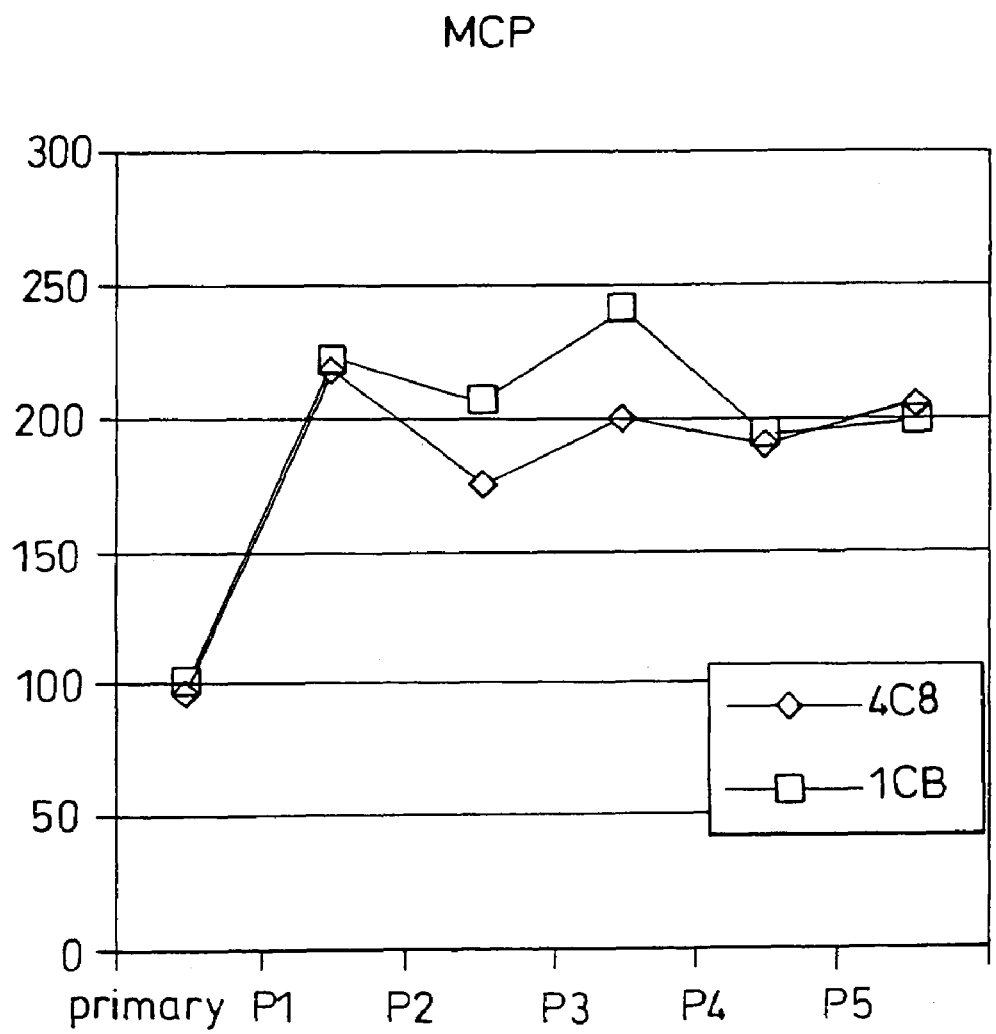

FIG. 23 shows the expression of pig CD59 on PAEC at different passages.

FIG. 24 shows the complement susceptibility of PAEC at different passages.

Figure 25:
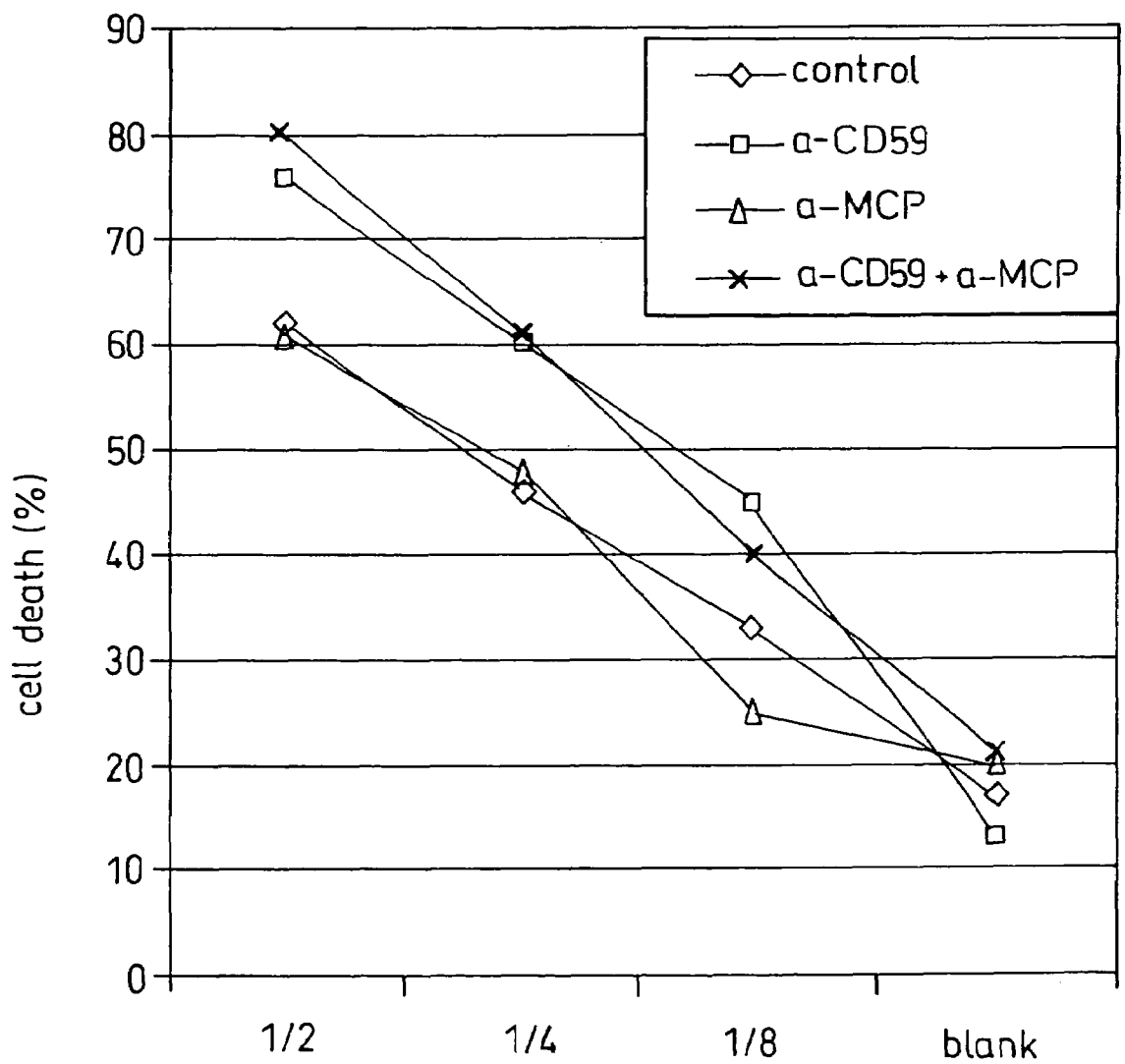

FIG. 25 shows the effect of blocking CD59 and MCP of C-susceptibility of PAEC.

Figure 26:
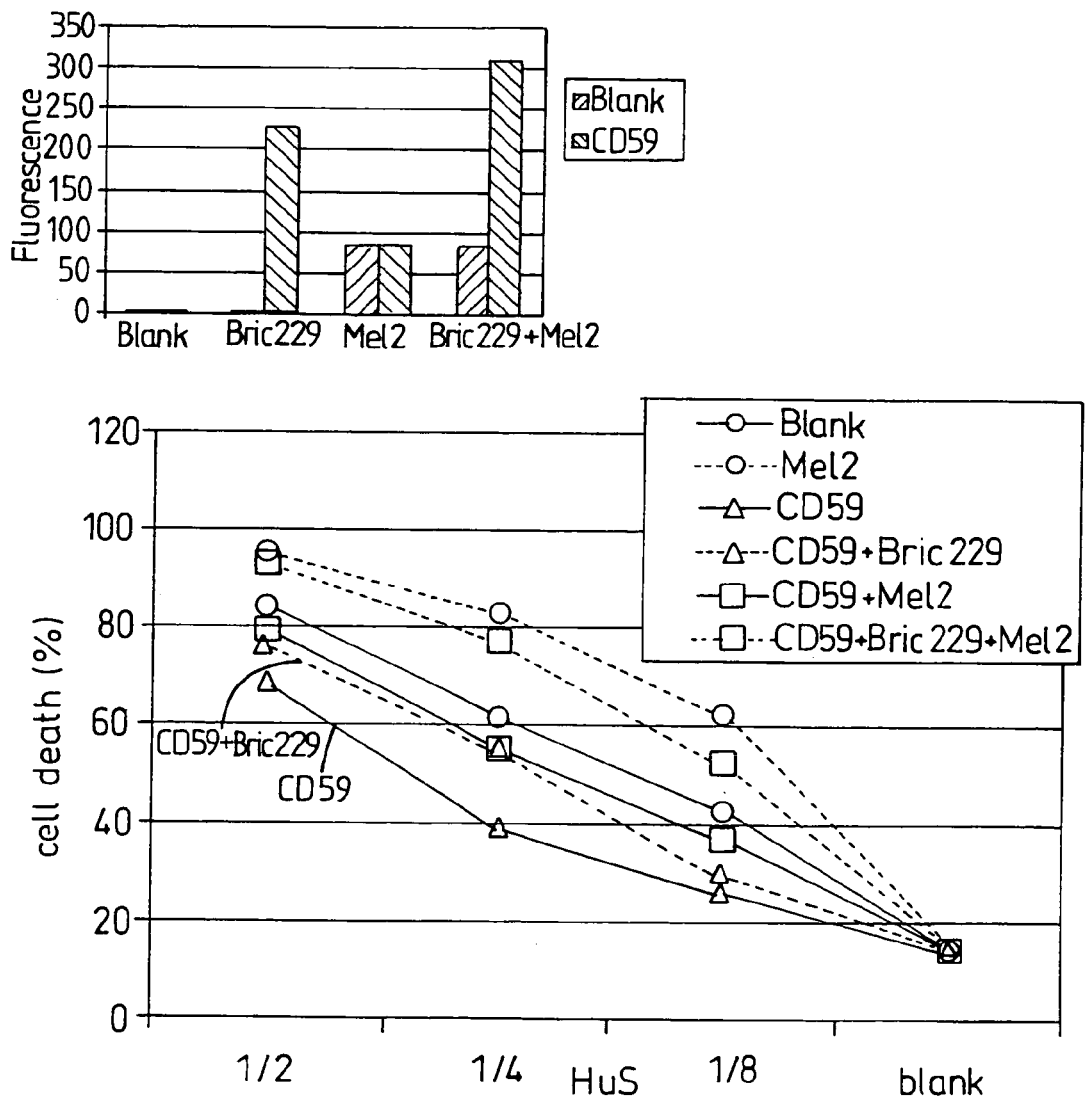

FIG. 26 shows the effect of incorporation of human CD59 into PAEC and the effect of blocking of human and pig CD59 on complement susceptibility.

Figure 3:
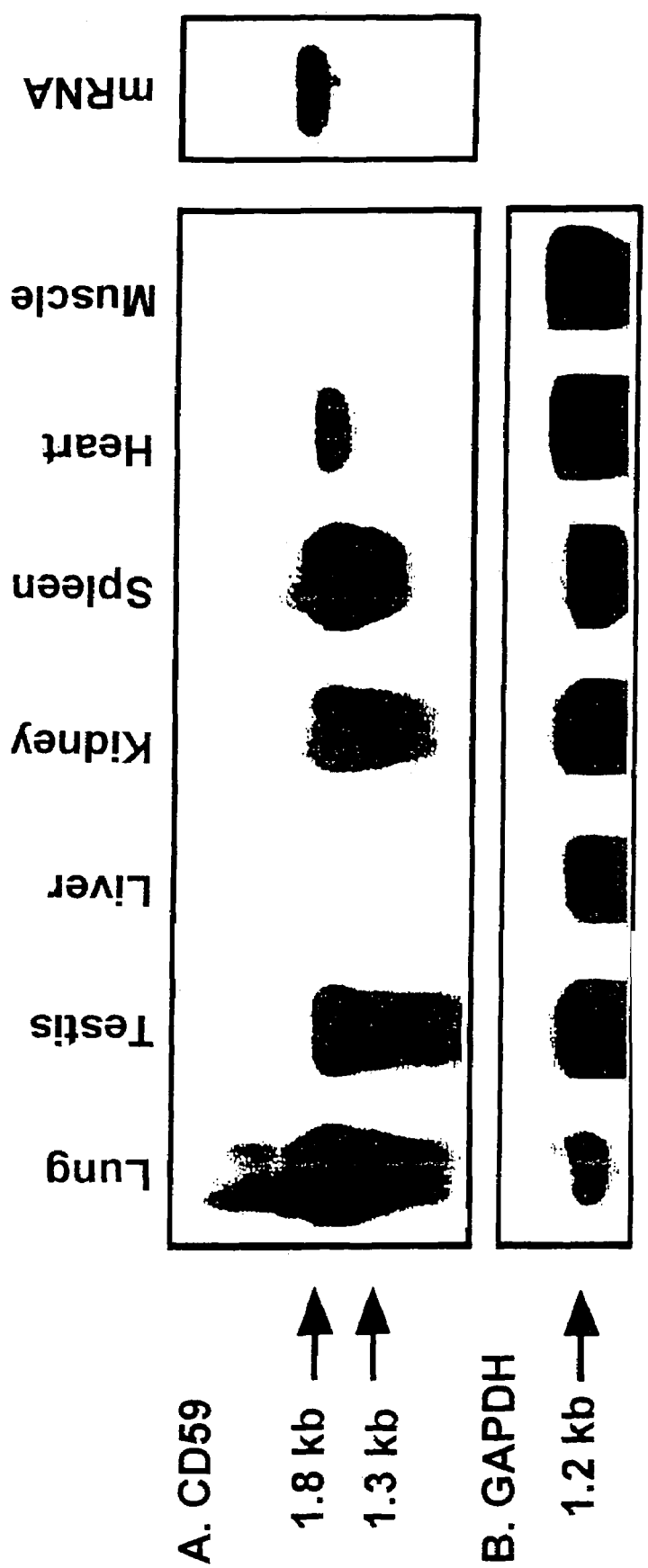

The initial portion of pig CD59 cDNA sequence was obtained by touchdown polymerase chain reaction (PCR) using two degenerate primers, the first designed from a region in the 38 amino acids of N-terminal sequence previously obtained, as mentioned above, the second designed based upon a region of high homology between human, rat and mouse CD59 near the C-terminus of the mature protein. The precise sequence of this latter region in pig CD59 was not known so the degeneracy of this primer was high to allow for many combinations. Once this internal stretch of sequence had been determined, gene specific primers were designed to complete the sequencing using the Rapid Amplification of cDNA Ends (RACE) approach. The 5' RACE reactions yielded a single specific product, while the 3' RACE reactions yielded four specific products. Two of these were sequenced and shown to be identical apart from the length of the 3' UTR; the two longer products were not sequenced but were likely also to be pig CD59 mRNA transcripts with longer 3' UTR. The suggestion that there are several different length transcripts of pig CD59 mRNA is supported by the Northern blots which show multiple specific bands of 0.8 kb, 1.3 kb, 1.8 kb and 3.0 kb (FIG. 3). This is similar to the situation for human CD59, which has five different length transcripts of 0.7 kb, 1.3 kb, 1.9 kb, 2.1 kb and 5.8 kb all due to alternative polyadenylation. In contrast, only a single transcript of 1.8 kb has been identified in rat CD59.

The full cDNA sequence (FIG. 2) (SEQ ID No. 2) contains a 84 bp 5' UTR, a 372 bp coding region, and a 312 bp 3' UTR, In the 5' UTR the 22 bp immediately 5' to the ATG start site is highly homologous between human, rat and mouse CD59, but is not conserved in the pig CD59 sequence. The Kozak sequence ($^{A}/_{G}$NNATG), recognised by ribosomes as the translational start site and thus required for protein expression, is present within the pig CD59 5' UTR sequence. The coding region consists of a 26 amino acid NH$_2$-signal peptide, with leucine known to be the first residue of the mature protein sequence from the above-mentioned amino acid sequence. Based on the consensus sequence for a phosphatidylinositol glycan anchor additional signal (GPI) J. Biol. Chem. 267 12168) it is predicted that the COOH-terminal 25 amino acids will be cleaved off and a preformed GPI-anchor attached to the Ser-73. The resulting 73 amino acid mature protein is 48% identical to human CD59, 46.5% identical to rat CD59 and 38% identical to murine CD59 at the amino acid level. There are two potential N-glycosylation sites in the pig CD59 sequence, at Asn-18 and Asn-71. The former site has previously been shown by protein sequencing to be occupied; it is unlikely that the latter site is occupied due to its close proximity to the GPI-attachment site, and thus the membrane.

It has been demonstrated by structural analysis of human CD59, that in the mature protein, the 12 amino acids at the C-terminus, following human residue Cys-64, have no defined structure and act like a "stalk", giving mobility to the molecule. The predicted GPI attachment site in pig CD59 is at Ser-73. The "stalk" of pig CD59 is thus only 7 amino acids in length, the same length as that of mouse CD59, but 5 amino acids shorter than that of human CD59, and 7 amino acids shorter than that of rat CD59. We have suggested that the short "stalk" of murine CD59 is responsible for the inefficient release of the molecule by PIPLC. Pig CD59 expressed on U937 is efficiently released by PIPLC treatment, although not to the same extent as human CD59 expressed on the same cell (FIG. 5). This indicates that the length of "stalk" has relatively little effect on the accessibility of the GPI anchor to the PIPLC enzyme.

Figure 6:
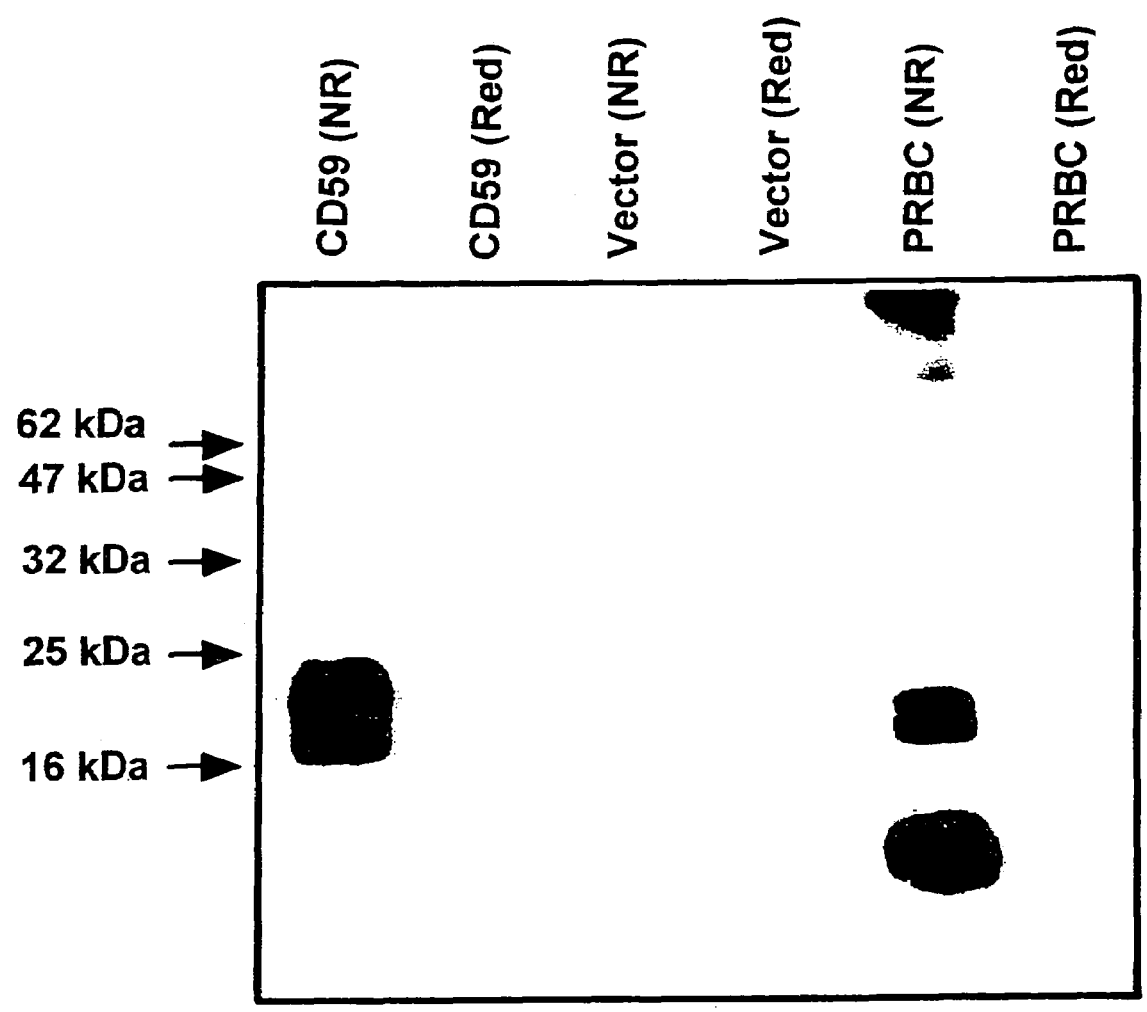

Pig CD59 was stably expressed in the CD59-negative human cell line U937. Western blotting showed that the expressed pig CD59 protein was of the predicted molecular weight and was glycosylated in a manner similar to that of human CD59 (FIG. 6). In fresh pig erythrocyte membranes there is an additional form of CD59 of molecular weight 10 kDa which may represent unglycosylated or deglycosylated CD59. Small amounts of deglycosylated CD59 have been observed on erythrocytes in other species, particularly after prolonged storage at 4° C. The abundance of this form on fresh pig erythrocytes suggests that the protein may be rather more susceptible to deglycosylation in vivo than CD59 in other species.

U937 cells stably expressing either pig or human CD59 showed a single homogeneous population of high expressors by flow cytometry using appropriate mAbs. This homogeneity of expression is mediated by the elongation factor 1α promoter in the expression vector, which varies little in its expression levels. Pig CD59 and human CD59 in the same vector and in the same cell type were therefore expressed at similar levels on the cell surface and could be directly compared.

The expressed pig CD59 inhibited lysis by complement from a variety of species, as previously reported with CD59 purified from pig erythrocytes (van den Berg et al J. Immunol.

152 4095 (1994)). The pattern and extent of inhibition was almost identical to that obtained with human CD59 expressed in the same cell line. Both pig and human CD59 were very effective at inhibiting pig, human and sheep complement and less effective at inhibiting rodent complement (FIG. 7). These data suggest that the residues involved in species selectivity are well conserved between human and pig CD59, but less so in rodent CD59s. In studies of human-rat CD59 chimaeras, the region of human CD59 between residues 40 and 66 has been implicated as conferring species selectivity between human and rat CD59. Within this region are several residues conserved between human CD59 and pig CD59, but not conserved in rat and mouse CD59. Residues Phe-47 and Lys-66 (human numbering) are conserved (Ala/Gly and Ala/Phe respectively in rat/mouse) and there are conservative substitutions at human residues 43 (Glu→Asp), 51 (Thr→Ser) and 65 (Lys→Arg) (Ser/Ser, Leu/Met and Gln/Gln respectively in rat/mouse). These residues may therefore be important in the species selectivity of CD59 molecules.

Expression of CD59 analogues at high levels in a CD-59-negative cell line provides a model for the situation in transgenic pigs developed for xenotransplantation, where human CD59 has been expressed at high levels in certain organs in order to inhibit the damage during complement attack by human serum. Pig CD59 and human CD59, expressed at high levels in the human U937 cell line, inhibit human complement to a similar extent, indicating that it is the level of expression rather than the species of CD59 which is important in conferring protection.

The above data indicate that hyper-expression of an endogenous CRP such as pig CD59 in the transplanted organ would provide protection equal to that conferred by hyper-expression of human CRP in the pig. Hyper-expression of the endogenous inhibitors could be achieved by transgenesis, but there may be alternative ways of achieving this end, for example, by identifying agents which cause a large, sustained upregulation of CD59 expression on donor endothelial cells.

The present invention will now be illustrated and specifically described in the following examples.

EXAMPLES

Materials and Methods used in the Examples

Materials

Molecular Biology. All general reagents were from Sigma Chemical Co. (Poole, UK) unless otherwise stated. Ultraspec RUA isolation media was from Biotecx (Houston, USA). Rnase H Superscript reverse transcriptase, Rnase H, terminal dioxynucleotide transferase and all restriction enzymes were from Life Technologies (Paisley, UK). Nick™ columns for radioactive probe purification, Taq polymerase and buffers were from Pharmacia (Milton Keynes, UK); Vent DNA polymerase was from New England Biolabs (Veverly Mass.); and dNTPs were from Bioline (London, UK). RNase inhibitor rRnasin® and pGEM-T vector kit were from Promega (Southampton, UK). Geneclean II DNA purification kit was from Anachem (Luton, UK) and plasmid purification kits were from Qiagen (Dorking, UK). Hybond-N nylon membranes, Rapid-Hyb buffer, rediprime DNA labelling system and [α-$^{32}$P]dCTP were from Amersham International (Little Chalfont, UK). oligonucleotide primers were synthesised in house on an ABI Model 394 synthesiser (Applied Biosystems, Warrington, UK).

Tissues, Cells and Sera. Animal sera were obtained fresh from the animal facility of the University of Wales College of Medicine and stored at −70° C. Normal human serum was obtained from healthy volunteers and stored at −70° C.

The human promonocyte U937 cell line was originally obtained from the European Collection of Animal Cell Cultures (ECACC, Porton Down, UK). The derivation of a CD59-negative subclone is described in Immunology 81 637 et seq. (1994). Cells were cultured in RPMI 1640 medium (Life Technologies), Paisley, UK) supplemented with 10% FCS, 4 mM glutamine, 2 mM sodium pyruvate, 100 IU/ml penicillin, 100 IU/ml streptomycin and 2.5 µg/ml amphotericin. Pig endothelial cells isolated from pig aorta by standard methods were a kind gift from the Department of Cardiology, University of Wales College of Medicine. All tissues for Northern blots were obtained fresh from the local abattoir.

Antibodies. High titer polyclonal antiserum against CD59-negative U937 cells was raised in rabbits using standard procedures. The monoclonal antibodies to pig CD59 (MEL-1 and MEL-2) were generated in house, as described in detail below. BRIC229 (α-human CD59 mAb) was from International Blood Group Reference Laboratory (IBGRL. Bristol, UK). Goat anti-mouse/IgG-horseradish peroxidase (GαM-HRPO) was from Bio-Rad (Hemel Hempstead., UK). Goat anti-mouse/IgG-phycoerythrin (GαM-PE) was from DAKO (Denmark).

Monoclonal Antibody Production

Monoclonal antibodies to pig CD59 were made by standard protocols. (Galfre, G. Milstein, C, (1981) Preparation of Monoclonal Antibodies: strategies and procedures. Methods Enzymol.73.3) Briefly, BALB/C mice were immunized subcutaneously with pig erythrocyte ghosts in Freund's Complete Adjuvant (FCA) Animals were boosted twice by intraperitoneal (i.p.) injection of highly purified pig CD59 prepared by preparative electrophoresis 3 weeks and 14 weeks later, with and without Freund's Incomplete Adjuvant (FIA) respectively. A third and final i.p. boost of pig erythrocyte ghosts was administered 37 weeks after the initial immunization. Animals were sacrificed, spleens removed, spleen cells harvested and fused with the mouse myeloma cell line SP2/0 9 days after the final boost. Positive clones were selected by incubation of hybridoma supernatants from individual wells with U937 cells expressing or not expressing pig CD59 followed by determination of bound antibody by flow cytometry, and by Western blotting using cell lysates of the U937 transfected cells. Three separate positive wells were taken through secondary and tertiary cloning and then grown in bulk. Three monoclonal antibodies were produced, one IgM (MEL-1) and two IgG1 (MEL-2 and MEL-3). Immunoglobulins were isotyped using the Isostrip Kit (Boeringher Mannheim, Mannheim, Germany) or the Isotyping Kit (Sigma Chemical Co.) MEL-2 and MEL-3 were chosen for further studies and for purification purposes.

Purification of Immunoglobulins

The IgG's were purified using a protein A column (Prosep A beads, Bioprocessing, Durham, UK) Protein-concentration was determined using a Coomassie Blue Protein assay (Pierce, U.K.).

Reverse Transcription

Total RNA was extracted from cultured pig endothelial cells using the Ultraspec RNA isolation system. The RNA was reverse transcribed by incubation with 500 U Superscript RNase H-Reverse transcriptase at 20° C. for 10 minutes, then 42° C. for 90 minutes in the presence of 50 mM Tris-HCl, 75 mMKCl, 3 mM MgCl$_2$, 5 µM DTT, 60 U rRNasin® and 2 mM dNTPs, in a total volume of 30 µl.

PCR Amplifications

All PCR reactions were carried out in a OmniGene thermal cycler (Hybaid, Middlesex, UK). Taq DNA polymerase (2.5 U) was used to amplify the DNA in the presence of $NH_4^+$ buffer (16 mM $(NH_4)_2SO_4$, 67 mM Tris-HCl, 0.01% Tween-20), 1 mM $MgCl_2$, 0.08 mM dNTPs and appropriate primers, in a total reaction volume of 50 µl overlaid with mineral oil.

Degenerate PCR Amplification

Random hexamers of DNA (500 ng) were used to prime the initial reverse transcription of 10 µg total RNA to produce a template for the PCR amplification.

Figure 1:
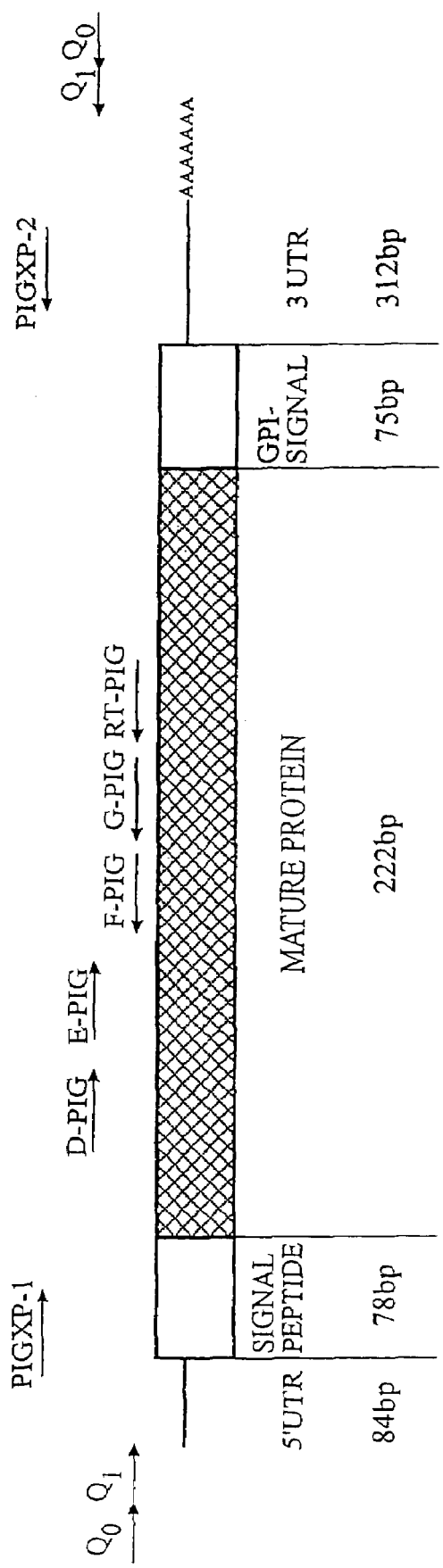

Degenerate primers A- PIG ($TGC/_TTAC/_TAAC/_TTGC/_T AT^A/C/_TAA$) (SEQ ID No. 3) and C-PIG ($AG^G/_ATCC/_T TC/_TC/_TTG/_TG/_ACA^G/_ACA$) (SEQ ID No, 4) were derived from amino-terminal protein sequence corresponding to residues 3-8 (CYNCIN) of pig CD59 and a region of high interspecies homology of all known CD59 sequences close to the C-terminus corresponding to residues 63-68 (SEQ ID NO: 23) (CCKKDL) in human CD59. The approximate positions of these primers are shown in the schematic diagram of the pig CD59 cDNA (FIG. 1). A variation on the touchdown procedure of Don et al Nucleic Acids Res. 19:4008 was performed, with 500ng of each primer used in the amplification. A denaturation at 950° C. for 4 minutes was followed by initial cycling parameters of 94° C. for 30s, 54° for 40s and 72° C. for 45s. Thereafter the annealing temperature of the reaction was decreased 2° C. every second cycle from 54° C. to a touchdown of 40° C. at which temperature 25 cycles were carried out.

Derivation of the 3' End of Pig CD59 cDNA

The method used was a modification of the rapid amplification of cDNA (RACE) method described by Frohman, M. A. 1990 PCR Protocols: A Guide to Methods and Applications. Academic Press, London, pp 28-38). A poly-dT adaptor primer $Q_T$ (CCAGTGAGCAGAGTGACGAGGACTC-GAGCTCAAGCT$_{17}$) (SEQ ID No.5) (28 pmol) was used to reverse transcribe mRNA from 10 µg total RNA. $Q_T$ binds to the poly-A tails of all mRNAs thus priming reverse transcription and consequently adding an extra 35 bases of unique sequence to the cDNA end. Nested PCR was performed using primers specific for this unique sequence, $Q_0$ (CCAGTGAG-CAGAGTGACG) (SEQ ID No.6) and $Q_1$ (GAGGACTC-GAGCTCAAGC) (SEQ ID No.7) along with pig CD59 specific primers D-PIG (TGCACTACGGCCATGAATTG) (SEQ ID No.8) and E-PIG (TCGTTGAAGCCGTGC-CACCC) (SEQ ID No.9), designed from the cDNA sequence obtained from the degenerate primer PCR reaction. The positions of these primers are shown in FIG. 1.

In the first amplification 7% of the $Q_T$ primed cDNA was amplified using 25 pmols of primer $Q_0$ and the degenerate primer A-PIG, using touchdown PCR as above. In the second amplification a 1 µl aliquot of a 1:20 dilution of the first reaction was amplified using 25 pmol $Q_1$ and 25 pmol D-PIG with the following reaction conditions: 94° C. for 30 s, 54° C. for 1 minute (ramp 2.5) and 72° C. for 2 minutes for 30 cycles. In the third amplification a 1 µl of a 1:20 dilution of the second amplification was amplified using 25 pmol $Q_1$ and 25 pmol E-PIG with the following reaction conditions: 94° C. for 30 s, 58° C. for 1 minute (ramp 2.5) and 72° C. for 2 minutes for 30 cycles.

Derivation of the 5' End of Pig CD59 cDNA

A pig CD59 specific primer RT-PIG (AGGTCCTTCTTG-CAGCAGTG) (SEQ ID No.10) (6 pmol), derived from the cDNA sequence obtained from the degenerate PCR reaction, was used in the reverse transcription of the 5' end of the mRNA from 10 µg total RNA. After reverse transcription the RNA was degraded by incubation for 20 minutes at 37° C. with 2.5 U RNase H. The single stranded cDNA generated by reverse transcription was purified from primers and enzyme using the Geneclean II kit (Anachem). The purified cDNA was polyadenylated at its 3' end by incubation with 10 U terminal deoxynucleotide transferase (Life Technologies) in the presence of 5 mM ATP at 37° C. for 5 minutes, then 65° C. for 10 minutes. The mixture was the heated to 95° C. to denature the enzyme and 5% of the resulting polyadenylated single-stranded cDNA was used directly in the first PCR amplification. The poly-A tail generated was used to initially amplify the cDNA with the adaptor primer $Q_T$ followed by further amplification using the primers $Q_0$ and $Q_1$ and the pig CD59 specific primers G-PIG (CTTCTCCGCTAG-GTTTCTCG) (SEQ ID No.11) and F-PIG (GCATTCATC-GAACCTCCAAC) (SEQ ID No.12), which were designed from the cDNA sequence obtained from the degenerate PCR reaction.

In the first amplification the cNDA was amplified using 3 pmol $Q_T$ primer, 25 pmol $Q_0$ and 25 pmol G-PIG, using the following conditions: 96° C. for five minutes, 50° C. for 2 minutes (ramp 2.5) and 72° C. for 40 minutes, followed by 30 cycles of 94° C. for 1 minute, 58° C. for 1 minute and 72° C. for 2 minutes.

A 1 µl aliquot of a 1:20 dilution of the first reaction was reamplified using 25 pmols of each of the nested primers $Q_1$ and F-PIG using the following conditions: 94° C. for 1 minute, 58° C. for 1 minute (ramp 2.5) and 72° C. for 2 minutes for 30 cycles.

Cloning and Sequencing of PCR Products

Purified PCR products were ligated into the pGEM-T vector cloning site (insert:vector molar ratio 3:1) by incubation with 1 Weiss Unit of T4 DNA ligase (16° C. for 16 hours) in a total volume of 10 µl of 30 mM Tris-HCl (pH 7.5), 10 mM $MgCl_2$, 10 mM DTT and 1 mM ATP. A 1 µl aliquot was then electroporated into electrocompetent DH5α *Escherichia coli* at 2.5 kV, 25 µFD and 200Ω using a Bio-Rad Genepulser. The bacteria were then grown on Luria-Bertani/Agar plates and selected for by ampicillin resistance and by blue/white colour selection using X-Gal (5-bromo-4-chloro-3-indolyl β-D-galactoside) substrate. Positive colonies were picked, a portion retained for checking insert size and the remainder replated on LB/Agar plates. The retained portion was boiled in 20 µl water for 10 minutes to release and denature the plasmid, then put on ice for 10 minutes. PCR was performed using 5 µl of boiled bacteria as the template and T7 and SP6 primers which flank the insert site in the vector, and the reaction resolved on agarose gels. Colonies with-inserts of the correct size were expanded for 16 hours in 5 mls LB broth containing 50 µg/ml ampicillin at 37° C. and the plasmids purified using the QIAprep spin plasmid kit (Qiagen).

Automated sequencing was carried out in house using an ABI model 377 DNA sequencer. (Applied Biosystems, Warrington, UK).

Southern and Northern Blot Analysis

Probes for Southern and Northern blot analysis were generated from double-stranded pig CD59 template DNA isolated by elution from a low melting point agarose gel. The DNA concentration was measured and adjusted to 550 ng/ml prior to denaturation at 95° C. for 2 minutes and quenching in ice water. Lyophilised Redi-prime constituents were reconstituted in 45 µl template DNA, 5 µl (50 µCi) of [α-$^{32}$P]dCTP added and the mixture incubated at 37° C. for 1 hour. The product was purified from remaining nucleotide using a Nick column (Pharmacia, Milton Keynes, UK) and stored at 4° C.

Total RNA for Northern blot analysis was purified from whole tissues and from cultured pig aortic endothelial cells using the Ultraspec RNA isolation system. The PolyATract mRNA isolation system (Promega, Southampton, UK) was used to purify messenger RNA from cultured endothelial cells. Total RNA (10 µg) or mRNA (2 µg) was run on denaturing agarose gels and transferred overnight to Hybond,N nylon membrane using capillary action. For Southern blot analysis PCR products were run on agarose gels and transferred to Hybond-N using capillary action. The nucleic acids were crosslinked to the membrane by U.V. irradiation (U.V. Stratalinker, Stratagene UK). The membrane was prehybridised in Rapid-Hyb buffer at 65° C. for 1 hour before addition of the radiolabelled probe which had been denatured at 95° C. Southern blots were hybridised with a 200 bp probe generated from the pig CD59 cDNA cloned using degenerate primers. This was hybridised for 3 hours at 65° C., washed 2×5 minutes with 0.2×SSC/0.1% SDS at 65° C., and exposed to X-ray film for up to 6 hours at −70° C. Northern blots were hybridised for 16 hours at 65° C. with a 610 bp probe generated from the pig CD59 coding sequence cloned in the expression vector. This was washed at room temperature with a 2×10 minutes 2×SSC/0.1% SDS and 2×10 minutes 1×SSC/0.1% SDS, and exposed to X-ray film for up to 48 hours at −70° C.

Construction of Eukaryotic Expression Vector for Transfection of Pig CD59

The eukaryotic expression vector pDR2EF1α was a gift from Dr. I. Anegon (INSERM U437, Nantes, France) Transplantation 58:1222. PDR2EF1α contains hygromycin resistance gene, allowing the selection of stable colonies, and the powerful polypeptide chain elongation factor 1α promoter to generate high expression levels Nucleic Acids Res. 18:5322. From the full length pig CD59 sequence two primers, PIGXP-1 (GGTTCTAGAGTAGCGCTGCAGCCGGAC) (SEQ ID No.13) and PIGXP-2 (GGTGGATCCTTCTCTGC-CAACAGGCCT) (SEQ ID No.14), were designed to PCR amplify the entire coding region, including the Kozak sequence, essential for ribosomal recognition of the translational start site. These primers contain Xba-1 and BamH1 restriction sites respectively. These sites are also present as unique sites in the insertion region of the expression vector, allowing correct orientation of the insert. PCR product and vector were restriction enzyme digested prior to ligation. The presence and fidelity of the pig CD59 in the vector was confirmed by DNA sequencing.

Transfection of CD59-negative U937 Cell Line

The promonocytic cell line U937 was transfected by electroporation with the empty expression vector, the expression vector containing pig CD59 or vector containing human CD59 J.Immunol. 158:1692. U937 cells growing in log phase were washed 3× with sterile PBS and resuspended in ice-cold RPOMI-1640 from Gibco at a final concentration of 3×10$^7$ cells/ml. Cells (450 µl) were added to a sterile cuvette with 10 µg of super coiled plasmid. The cuvette was placed on ice for 5 minutes and electroporated at 270V and 960 µF using the Bio-Rad Genepulser with capacitance extender. The cuvette was then placed on ice for a further 30 minutes. Cells were returned to sterile culture flasks and cultured for 24 hours in 10 ml fresh RPMI containing 10% FCS. Cells were washed once in sterile 0.9% NaCl and resuspended in selection medium (RPMI containing 0.7 mg/ml hygromycin B; Boehringer Mannheim, Lewes, UK). Selection medium was changed every two days for approximately 2 weeks, by which time all the non-transfected control cells had died. Transfected cells were then maintained in RPMI containing 0.1 mg/ml hygromycin B.

FACScan Analysis

Cells were harvested, washed three times in PBS/1% BSA, and resuspended at 10$^6$ cells/ml in VBS (Veronal buffered saline)/1% BSA. All steps were conducted on ice. Cells (10$^5$) were incubated with appropriate mAbs at 10 µg/ml for 30 minutes, washed three times with VBS/1% BSA, and incubated for 30 minutes with a 1/100 dilution of goat anti-mouse/IgG phycoerythrin. Cells were washed three times in VBS/1% BSA, and fluorescence was measured using a FACScalibur flow cytometer (Becton-Dickinson, San Jose, USA).

To examine the effects of treatment with phosphatidylinositol-specific phospholipase C (PIPLC), cells were washed and resuspended at 3×10$^6$/ml in PBS containing PIPLC (0.4 U/ml, Peninsula Laboratories, St. Helens, UK). After an incubation for 30 minutes, cells were washed and CD59 expression measured by flow cytometry using the above protocol.

Functional Assays

To eliminate the interfering effects of antibiotics, stably transfected cells were cultured in the absence of hygromycin B for seven days before assessment of sensitivity to complement lysis. Cells growing in log phase were harvested, washed three times in PBS, resuspended in RPMI/10% FCS at 10$^7$ cells/ml and loaded with calcin-AM (Molecular Probes, Oregon, US; 2 µg/ml) for 30 minutes at 37° C. Cells were washed twice with,PBS and resuspended in a 1/5 dilution of heat-inactivated rabbit anti-U937 polyclonal antiserum in VBS/1% BSA for 15 minutes at 4° C. Cells were washed once in PBS and resuspended in VBS/1% BSA containing the appropriate dilution of fresh serum. The mixture was incubated for 30 minutes at 37° C., after which the cells were pelleted, the supernatant removed and retained for fluorescence measurement using the WellFluor system (Denley, Sussex, UK). The cells were then incubated for a further 15 minutes in 0.1% Triton X-100, to release any remaining calcein. Residual cell debris was pelleted and the supernatant removed for fluorescence measurement. Percentage lysis by serum was calculated as follows:

$$\% \; lysis = \frac{\text{calcein released by complement}}{\text{calcein released by complement+}} \times 100$$
$$\text{calcein released by detergent}$$

SDS-PAGE and Western Blotting of Cell Lysates

Samples were run on 15% SDS-PAGE gels under non-reducing conditions, blotted onto nitrocellulose and blocked with 5% dried milk/PBS. The blots were incubated for 1 hour at room temperature with primary antibodies (10 µg/ml in 5% dried milk/PBS), washed three times in PBS/0.1% Tween-20, incubated with goat anti-mouse/IgG horseradish peroxiase (1/1000 in 5% dried milk/PBS), and washed with PBS/0.1% Tween-20, and twice with PBS. Blots were developed using Supersignal Chemiluminescent Substrate (Pierce, Rockford, Ill.).

Example 1

PCR Cloning of Pig CD59 cDNA

Degenerate PCR using primers A-PIG and C-PIG produced four PCR products, ranging in length from 150 bp to 400 bp. All the PCR products were cloned into the pGEM-T vector and electroporated into DH5α bacteria. From the resultant colonies, 20 were screened by PCR using T7 and SP6 primer sites in the vector which identified 6 colonies containing an insert of the predicted length (200 bp) These 6 colonies were grown up and the plasmids purified and sequenced. All were identical. The amino acid sequence derived from this cDNA sequence was 100% identical to the above-mentioned partial amino acid sequence for purified pig CD59, thus confirming that the sequence was correct.

This sequence was then used to design primers in order to PCR amplify the 3' and 5' ends (primers summarised in FIG. 1). 5' RACE, using primers $Q_0$ with G-PIG, followed by a second amplification using primers $Q_1$ with F-PIG, produced a strong 300 bp PCR product which Southern blotted with a probe derived from the 200 bp of known sequence. This was cloned, sequenced and confirmed to be the 5' end of the cDNA. 3' RACE produced four PCR products of 350 bp, 500 bp, 1 kb and 1.3 kb, all of which hybridised on a Southern blot with the 200 bp probe. The 350 bp and 500 bp products were cloned and sequenced, and were confirmed to contain the 3' end of pig CD59, differing only in the length of the 3' UTR. The longer products were not analysed further, but were thought to be likely to represent yet longer transcripts of pig CD59.

Reverse transcriptase PCR of the full-length cDNA for ligation into the expression vector produced a single 629-bp is product. After ligation and electroporation, 12 clones were picked and the plasmids purified and sequenced of the 12 clones, 10 gave the identical sequence, the other two, differing by one or two bases.

The full length cDNA sequence is shown in FIG. 2. The sequence encodes a 84 bp 5' UTR, a 26 amino acid $NH_2$-signal peptide, and a 98 amino acid coding region including two putative N-glycosylation sites at N-18 and N-71 and a glycosyl phosphatidylinositol (GPI) anchoring signal. The predicted site of GPI anchor addition based upon the known requirements for anchor addition is at S-73. The mature protein sequence is 48% identical to human CD59, 46.5% identical to rat CD59, and 38% identical to murine CD59. A comparison of the sequences of the various CD59 analogues is shown in FIG. 4.

Example 2

Northern Blot Analysis

Northern blot analysis of mRNA from porcine endothelial cells indicated that pig CD59 had two major transcripts of 1.8 kb and 1.3 kb, which are clearly visible in FIG. 3; two faint bands of 0.8 kb and 3.0 kb were consistently seen on a longer exposure. The 3' UTR of the longer of the sequenced clones was 312 bp which correlates with the 0.8 KbmRNA species, but Northern blot analysis demonstrates that mRNA species with even longer 3' UTR were also present.

Northern blot analysis was also performed on total RNA freshly extracted from pig tissues (FIG. 3). Expression of pig CD59 was found in all tissues, albeit at different levels. Expression was highest in lung and spleen and was low in liver and skeletal muscle. The relative expression of the two major bands at 1.8 kb and 1.3 kb also varied between tissues, lung expressing similar amounts of the two, spleen rather more of the larger band while testis, cardiac and skeletal muscle expressed almost none of the lower band. Probing for GAPDH confirmed that similar amounts of RNA had been loaded for all tissues with the exception of lung where rather less RNA was loaded.

Example 3

Expression of Pig CD59 in a CD59-Negative Cell Line

Stable populations of U937 cells expressing pig or human CD59 were generated as discussed above. Expression was confirmed using the mAb BRIC229 (IgG2b) for human CD59, and a new mAb raised against pig erythrocytes and conclusively shown to recognise pig CD59 (MEL-2 IgG1). Uniform, high level, stable expression was obtained for both proteins (FIG. 5). The pDRΔEFlα vector was chosen because it was reported to give comparable levels of expression of different cDNAs in a given cell type. It was therefore anticipated that similar levels of expression of human and pig CD59 would be achieved.

Neither of the mAbs recognized vector control cells, BRIC229 was negative on pig CD59-transfected cells. Although precise comparison of expression based upon staining with different reagents is not possible, the data suggest that pig CD59 and human CD59 were expressed at similar levels. Expression of pig CD59 on transfected U937 cells was sixfold that of endogenous CD59 on the endothelial cell line PLECT, as assessed by flow cytometry (data not included). We have shown previously that expression of human CD59 on U937 cells using this vector was approximately 10-fold higher than levels obtained on cells endogenously expressing the protein (endothelial cells and K562 cell-line).

Treatment of transfectants with PIPLC decreased expression of pig CD59 by 50%, as assessed from the mean cell fluorescence of the population, confirming that the protein was GPI anchored (FIG. 5a). This decrease in expression following PIPLC treatment is similar to that of human CD59 expressed on the same cell type, which decreased in mean cell fluorescence by 65% (FIG. 5b)

Western blotting of pig erythrocyte membranes using two different anti-pig CD59 mAb (MEL-1 IgM; MEL-2Ig1) revealed a broad band in the $M_r$ range of 16 to 22 kDa, and a second distinct band of 10 KDa, whereas blotting of pig CD59-expressing U937 cell membranes revealed a ladder of bands in the $M_r$ range of 17 to 23 kDa (FIG. 6). Western blots using isotype-matched controls for both Abs showed no reactivity with pig erythrocyte membranes, or pig CD59-expressing U937 cells. With the exception of the distinct band at 10 kDa in pig E, these patterns closely resemble those seen for CD59 from other species and represent variable glycosylation of the CD59 (1, 8-10). Preliminary data indicate that the 10-kDa erythrocyte band represents unglycosylated/deglycosylated CD59. Neither Ab recognized pig CD59 following reduction, a characteristic common to all anti-CD59 Abs in all species examined. There was no cross-reactivity of the anti-pig CD59 mAbs with human CD59 or of any of the available anti-human CD59 Abs (a panel of 10) with pig CD59 (data not included).

Example 4

Functional Activity of Pig CD59

The complement inhibitory activity of pig CD59 expressed on U937 s was evaluated, and compared with that of expressed human CD59, using a calcein-AM dye release assay. Transfectants expressing pig CD59, human CD59 or vector alone were antibody sensitised and incubated with sera from various species at different dilutions (FIG. 7). All sera, except mouse and sheep, lysed the sensitised vector control cells readily, averaging 80% lysis at a 1/10 dilution. Mouse and sheep sera gave a maximal lysis of 56% and 67% respectively at a dilution of ¹/₁₀. Expressed human CD59 markedly inhibited lysis by human, pig and sheep complement, but only moderately inhibited lysis by rodent complement. Expressed pig CD59 showed a pattern of protection almost identical to that of human CD59 for all species tested. In particular, pig CD59 and human CD59, expressed at similar levels in the same cell type, were equally effective at inhibiting lysis by human complement. The anti-pig CD59 mAb MEL-1 blocks function of this molecule. Preincubation of pig CD59-expressing cells with this antibody effectively eliminated the protective effect, confirming that inhibition was due to the expressed pig CD59 (FIG. 7).

Example 5

Hyper-expression of Pig CD59 in Pig Endothelial Cells and Cell Lines

Figure 8:
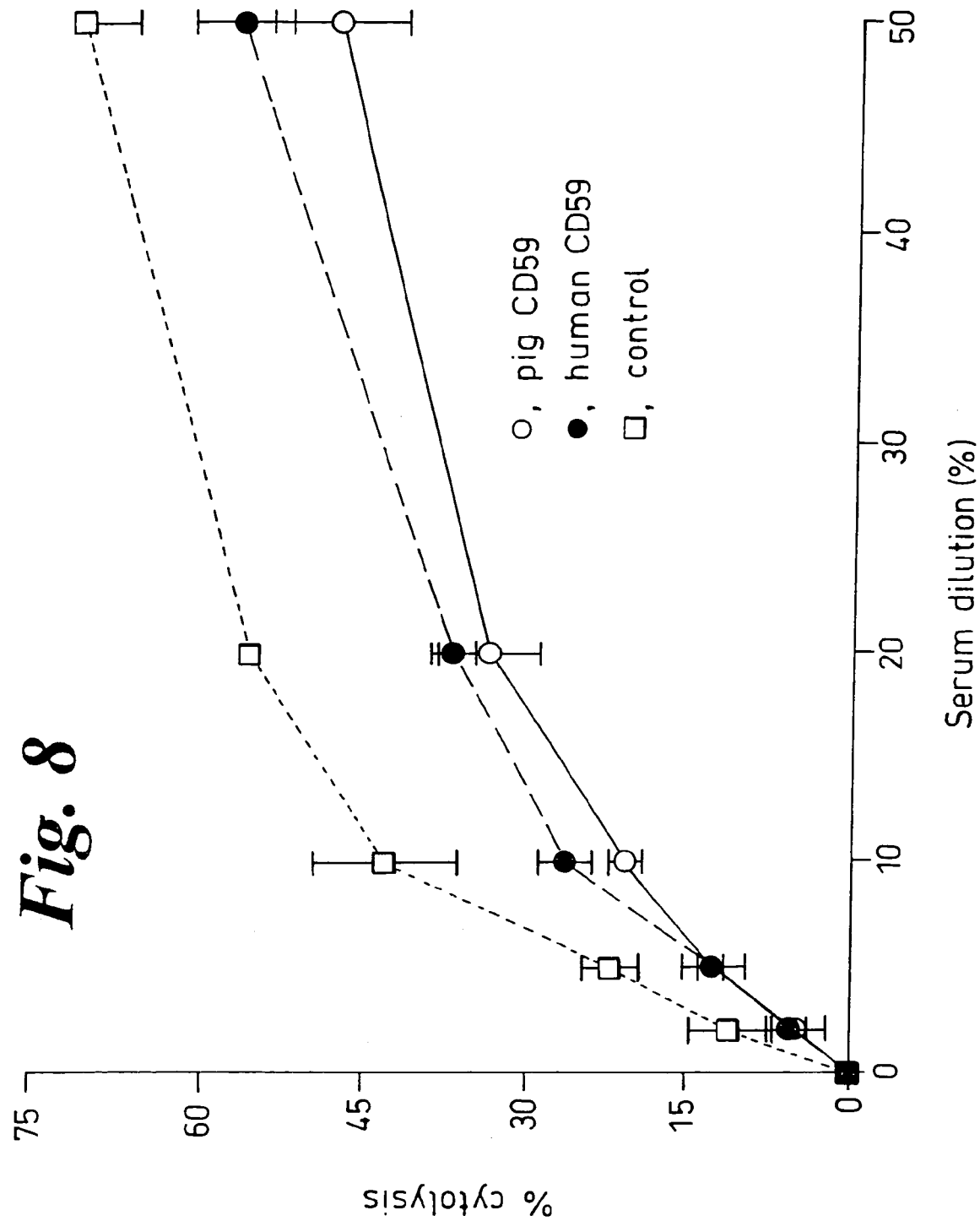
FIG. 8 is a graph comparing the human complement lytic sensitivity of a pig endothelial cell line expressing pig CD59 or Human CD59.

Pig CD59 was hyper-expressed in the pig endothelial cell line PLECT and in pig kidneys and testis cell lines essentially as described in Example 3. For comparison Human CD59 was hyper-expressed in the same lines. The extent of hyper-expression was typically 4-10-fold in comparison with endogenous expression on PLECT cells as assessed by flow cytometry. The human complement lytic sensitivity of the PLECT cells was measured and the results shown in FIG. 8. PLECT cells hyper-expressing pig CD59 are protected from lysis by human complement at least as well as PLECT cells expressing human CD59. These studies indicate that hyper-expression of a pig CRP in pig endothelium provides protection against damage by human complement which is at least as great as that conferred by hyper-expression of the equivalent human CRP. Similar results were obtained with the other porcine cell lines.

Example 6

Figure 9:
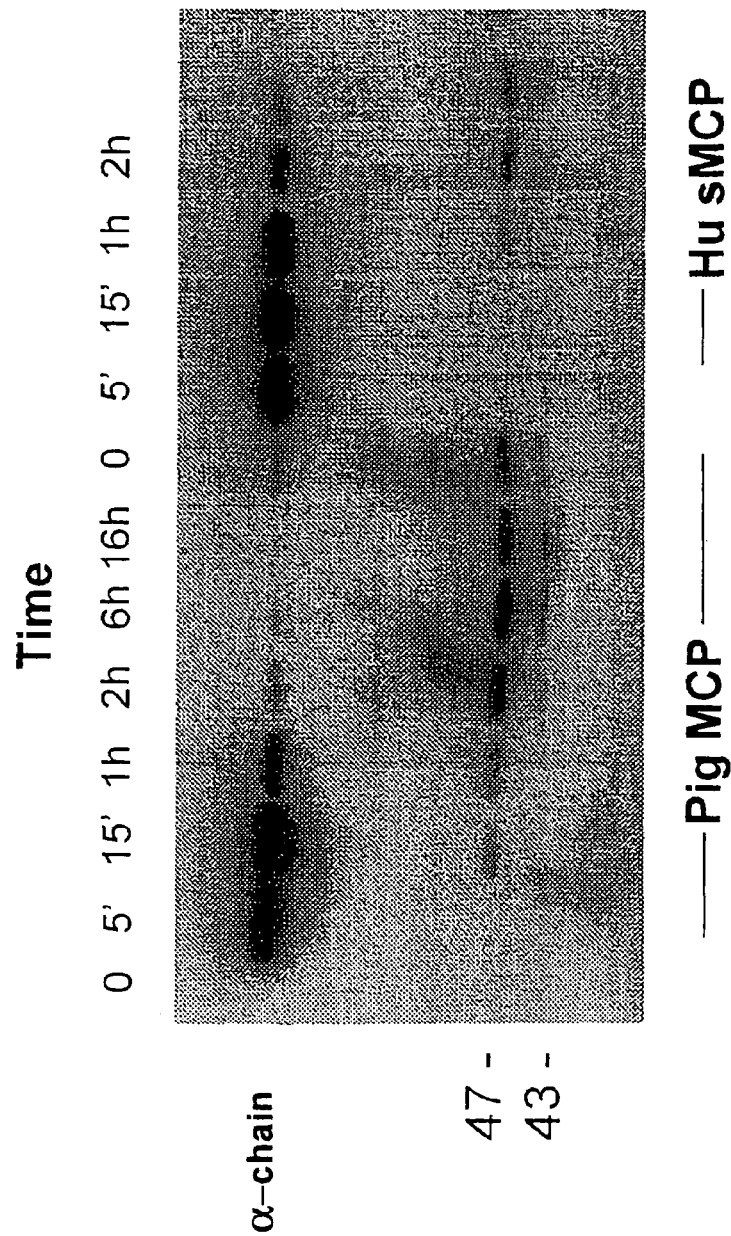
FIG. 9 is a Western blot comparing the time course of cofactor activity of pig MCP and human sMCP.

Comparison of Pig MCP and Human sMCP 500 ng of human C3 was incubated for various times at 37° C. with 50 ng of human factor I and 50 ng pig MCP or human sMCP. The time course of cofactor activity was observed by Western blotting, probed with anti-human C3C, and the results shown in FIG. 9.

Figure 10:
FIG. 10 is a Western blot comparing the dose/response cofactor activity of pig MCP and human sMSP.

500 ng of human C3 was incubated with 50 ng of human factor I and various amounts of pig MCP or human sMCP for 16 hours at 37° C. A Western blot of reduced samples was probed with anti-human C3c, and the results shown in FIG. 10. From this it will again be seen that pig MCP is a better cofactor than Human sMCP for cleavage of human C3 by human factor I.

Rabbit erythrocytes were incubated in the presence of human sMCP or pig MCP under classical or alternative pathway conditions to monitor the relative effectiveness of human sMCP and pig MCP as inhibitors of haemolysis by human serum. The results are shown in FIG. 11 from which it will be seen that pig MCP is a better regulator of the classical pathway of human complement than human sMCP and that pig MCP and human sMCP have similar activity in regulation of the human alternative pathway.

Example 7

Pig DAF

We have purified, using a mixture of classical and affinity methods, pig DAF from erythrocyte membranes and undertaken a partial characterisation of the purified protein. Referring to FIG. 12, pig DAF has been isolated from pig erythrocyte membranes by butanol extraction and passage of the butanol extract over a column of a weakly cross-reactive anti-human DAF monoclonal antibody (MBC-1) coupled to sepharose. The bound protein was eluted with 50 mM diethylamine, dialysed against PBS/Chaps and concentrated in an ultrafiltration cell. The protein has a molecular weight of approximately 65 kDa on SDS-PAGE gels, is GPI-anchored and spontaneously incorporates into the membrane of target erythrocytes. Incorporation of pig DAF into guinea pig erythrocytes conferred protection against lysis by pig serum whether activated through the classical or alternative pathways (FIG. 13). Incorporation into erythrocytes bearing C5b-7 sites failed to confer protection against lysis by C8/C9, confirming that the incorporated protein inhibited in the activation pathways (negative data not included). Initial tests on the species selectivity of pig DAF indicate that it readily inhibits human complement.

Amino-terminal sequencing was obtained through the first 14 residues, 12 of which were identified with confidence. The sequence (SEQ ID NO: 24) (DCGLPPxVPxAQPA) was highly homologous with the amino terminal sequence of human DAF. Partial cDNA sequence has been obtained using a PCR-based approach with a primer designed from the above sequence and from internal protein sequences predicted from comparisons of DAF sequences in human, mouse, rat (our original data) and guinea pig to be highly conserved. The cDNAs so obtained have been labelled and used as probes to isolate full-length pig DAF cDNA clones from a pig testis cDNA library.

Clones encoding pig DAF have been islated from this pig testis cDNA library using these probes.

Sequencing of clones has provided several cDNA sequences, all identical through the 3' region (encoding the signal peptide and the first three short consensus repeats (SCRs) of pig DAF) but thereafter, diverging. For examples, see clones pDAF-14 and pDAF-7 cDNA sequences (FIG. 14).

The predicted protein sequence of pig DAF through the first three SCRs is approximately 60% identical to the human DAF sequence (FIG. 15). Clone pDAF-7 contains, after these SCRs, a Ser/Thr/Pro-rich (STP) region homologous with the human STP-A and a carboxy-terminal sequence which may encode a glycolipid anchor but is also homologous with the membrane anchoring sequence in the transmembrane form of mouse DAF (FIG. 15).

Northern blotting of RNA extracted from pig tissues using a cDNA probe derived from the pig DAF sequence given in FIG. 14 identifies at least five specific bands in the majority of tissues (FIG. 16), indicating that multiple forms of the message exist. It is anticipated that forms of pig DAF containing a fourth SCR and/or glycolipid anchoring sequences, analogous to those in human DAF, will be found upon sequencing these other mRNAs.

The first three SCRs of pig DAF have been expressed as an Fc fusion protein in CHO (Chinese Hamster Ovary) cells. The recombinant protein, purified on protein A sepharose, has been used to immunise experimental animals for the purpose of producing specific antibodies. Preliminary functional analysis of the recombinant pig DAF-Fc reveals excellent complement inhibitory activity in classical pathway assays for both pig and human serum (FIG. 17).

A probe derived from the cDNA sequence given in FIG. 14 has been used in a radiation hybrid system to localise the gene for pig DAF to the long arm of chromosome 9.

Example 8

Induced Protection in PAEC Following Non-lethal Complement Attack

A propidium iodide uptake assay was used to monitor lysis of PAEC by human serum. PAEC were harvested from tissue culture flasks by incubation in PBS/1 mM EDTA and gentle scraping, washed in the complement-fixation diluent (CFD; Oxoid) and resuspended in CFD at $10^6$/ml. Portions were incubated with various dilutions (in CFD) of human serum (containing natural antibody) for the periods stated. The cells were then chilled to 4° C. and propidium iodide (PI) added (from a stock at 1 mg/ml in DMSO) to a final concentration of 10 µg/ml. Cells were analysed within 30 minutes by running on the flow cytometer, measuring fluorescence in the red channel (FL2). PI-positive (lysed) cells were highly fluorescent and easily distinguished from unlysed cells. The percentage of total cells in the highly fluorescent population was taken as percent lysis. Each set of conditions was run in triplicate.

Thus, PAEC (primary pig aortic endothelial cells) were incubated for one hour at 37° C. with concentrations of human serum (containing natural antibody) which did not cause significant amounts of lysis of the cells .(1/20, 1/30, 1/40; lysis always less than 10%). Control cells were subjected to a similar incubation but in the absence of serum. The cells were then washed and incubated for further 1 hour at 37° with various concentrations of serum in the range ½ to 1/256. Cell killing was measured by propidium iodide uptake. PAEC exposed to non-lethal complement attack at each of the three doses were much more resistant to lysis than unattacked control cells (FIG. 19a). Specific lysis was reduced to less than 20% of that in controls following non-lethal attack using serum at 1/20.

Flow cytometry was also used to measure expression of CD59 and MCP on PAEC, unattacked or attacked non-lethally with human serum. Cells were chilled to 4° C., washed once in cold FACS buffer (PBS containing 1% bovine albumin and 0.1% sodium azide), incubated with primary antibody (monoclonal anti-pig CD59 or anti-MCP, detailed earlier) at 10 µg/ml in FACS buffer for 1 hour at 4° C., washed twice in FACS buffer, incubated with secondary antibody (FITC-labelled anti-mouse IgG diluted 1:100 in FACS buffer) for 1 hour at 4° C., washed and resuspended in cold FACS buffer and analysed on the flow cytometer, measuring fluorescence in the green channel (FL1). The median fluorescence was taken as a measure of expression. All samples were run using identical machine settings. No significant change in expression of CD59 or MCP was detected following non-lethal complement attack and binding of human immunoglobulin was similarly unaffected (FIG. 19b).

These data support the concept that porcine endothelium can be rendered resistant to complement by first exposing to a non-lethal attack with complement. The resistant state is relatively long-lived (hours to days). The resistance observed was not accompanied by an increase in expression of CD59 or MCP.

Example 9

Induced Protection in PAEC Following a Period of Anoxic Stress

The appropriate gas mixture was prepared in 50 ml graduated syringes by first "drawing up" 47.5 ml $N_2$ from a cylinder of $O_2$-free $N_2$ and then "drawing up" a further 2.5 ml of air (all through a 0.2 µM filter). Small flasks containing PAEC (total volume 25 ml) were carefully filled from bottom up with the gas mixture and sealed. Following incubation for various intervals, cells were harvested, susceptibility to complement lysis was assessed by PI exclusion as described in Example 8 and expression of CD59 and MCP by flow cytometry as described in Example 8.

Thus, semiconfluent flasks of PAEC, grown in standard medium and environment (37° C., 95% air and 5% $CO_2$ were gassed with 5% air, 95% $N_2$, the flasks were sealed and incubated for intervals at 37° C. Cells were harvested, a portion removed for measurement of complement regulator expression and the remainder incubated with various amounts of human serum in a standard lytic assay format. Cells subjected to anoxia for periods of 12, 24 and 48 hours were more resistant to lytic killing by human complement than were control cells not subjected to anoxia (FIG. 20a).

Expression of CD59 and MCP and binding of human Ig were not significantly altered on PAEC subjected to anoxic stress when compared with controls (FIG. 20b).

These data support the concept that porcine endothelium can be rendered resistant to complement by first exposing to a period of anoxic stress. The resistance observed was not accompanied by an increase in expression of CD59 or MCP.

Example 10

Induced Protection in Human Cell Lines Following Growth Arrest Induced by Nutrient Deprivation or Cell Density Lytic susceptibility of K562 cells and U937 cells was assessed by propidium iodide uptake essentially as described in Example 8, except that a prior antibody sensitisation step (polyclonal anti-U937 antiserum, 1:10, 30 min at 40° C.) was necessary to obtain complement activation.

Expression of DAF, MCP and CD59 on K562 cells and U937 cells were assessed by staining with appropriate monoclonal antibodies, followed by FITC-labelled secondary antibody and analysis by flow cytometry, essentially as described in Example 8.

Subconfluent flasks of the human erythroleukaemia cell line K562 and the lymphoblastoid line U937 grown under standard conditions (medium containing 10% of fetal calf serum [FCS]), were subjected to nutrient deprivation by incubating in medium containing 1% FCS.

Alternatively, cells in medium containing 10% FCS were allowed to reach confluence and maintained at this density, with replacement of spent medium every 24 hours. Cells from both sets of condition were harvested after various periods and complement susceptibility assessed in a standard lytic assay.

Both nutrient-deprived and confluent cells remained viable for >72 hours but did not increase significantly in cell number during this period, confirming that they were growth-arrested.

Cells growth-arrested either by nutrient deprivation or by reaching confluence in culture were more resistant to complement lysis than were control cells maintained in log phase in standard culture conditions (FIG. 21a).

Expression of DAF and MCP were not significantly altered on K562 cells subjected to growth arrest when compared with controls, but CD59 expression was reduced on cells growth-arrested by nutrient deprivation (FIG. 21b).

These data support the concept that cells can be rendered resistant to complement by first exposing to a period of growth arrest. The resistance observed was not accompanied by an increase in expression of CD59, DAF or MCP.

Example 11

Induced Protection of PAEC by Treatment with Exogenous Stimuli

Medium was removed from the PAEC in semiconfluent culture, replaced with fresh medium containing the appropriate stimulus, phorbol myristate acetate at 10 nM final concentration, and returned to the incubator. At is various timepoints, cells were harvested and lytic susceptibility assessed by PI uptake essentially as described in Example 8.

Expression of CD59 and MCP was assessed by flow cytometry essentially as described in Example 8.

As shown by FIG. 18 the PAEC became more resistant to lysis by human or pig serum. A significant increase in resistance is achieved even after one day of treatment and further increases are seen up to three days of treatment.

Concomitant with the increase in resistance, expression of MCP on the PAEC rose two-fold but CD-59 expression is unaltered (FIG. 18).

These data support the concept that porcine endothelium can be rendered resistant to complement by treatment with exogenous chemicals, in this instance PMA. The resistance observed was not accompanied by an increase in the expression of CD59 or MCP.

Example 11

Expression and Function of Pig Complement Regulators on Porcine Aortic Endothelial Cell Aortic endothelial cells were harvested from fresh pig aortae and placed in culture. Expression of CD59 and MCP on primary cells and cells up to passage five was assessed by staining with specific monoclonal antibodies MEL2 and MEL3 (anti-CD59) or 4C8 and 1C5 (anti-MCP). The expression of CD59 fell steadily with increased passage number (FIG. 22) whereas MCP expression increased at later passage number (FIG. 23). Primary pig aortic endothelial cells (PAEC) were much more resistant to complement lysis than cells passaged in culture (FIG. 24). Blocking of endogenous CD59 with a monoclonal antibody (MEL2) markedly enhanced the susceptibility of PAEC to lysis by human serum whereas blocking of endogenous MCP had no discernible effect on lytic susceptibility (FIG. 25).

Incorporation of human CD59 into PAEC on which the endogenous pig CD59 had been blocked by monclonal antibody fully restored the resistance level of the PAEC to that of cells in which endogenous CD59 had not been blocked (FIG. 26).

These data provide further corroboration that CD59 is a major complement resistance factor in PAEC and that pig CD59 and human CD59 are of similar efficacy in protecting against human complement lysis of PAEC.

---

The invention claimed is:

1. An isolated DNA molecule coding for a polypeptide having the sequence of FIG. 2 (SEQ ID NO. 1) or its complementary strand.

2. An isolated RNA molecule comprising an RNA sequence corresponding to a DNA sequence according to claim 1.

3. A nucleic acid probe having a sequence according to claim 1, and optionally including a label.

4. A vector comprising the nucleic acid sequence of claim 1.

5. An isolated host cell transfected or transformed with a vector according to claim 4.

6. An isolated cell comprising a nucleic acid of claim 1 or 2.

7. An isolated cell comprising a vector of claim 4.

8. The cell of claim 7 wherein the cell is non-human.

9. A method for recombinantly expressing the polypeptide of SEQ ID NO: 1 comprising transfecting or transforming cultured host cells with a vector comprising a nucleic acid sequence encoding a polypeptide having the sequence of FIG. 2 (SEQ ID NO: 1), and culturing the cell under conditions so as to express the polypeptide having the sequence of FIG. 2 (SEQ ID NO: 1).

10. The method of claim 9, wherein the host cells are U937 cells or PLECT cells.

* * * * *